United States Patent
Marty et al.

(10) Patent No.: US 10,829,754 B2
(45) Date of Patent: Nov. 10, 2020

(54) PLASTIC DEGRADING PROTEASES

(71) Applicant: CARBIOS, Saint-Beauzire (FR)

(72) Inventors: Alain Marty, Toulouse (FR); Sophie Duquesne, Toulouse (FR); Marie Guicherd, Toulouse (FR); Marlene Vuillemin, Søborg (DK); Maher Ben Khaled, Toulouse (FR)

(73) Assignee: CARBIOS, Saint-Beauzire (FR)

( * ) Notice: Subject to any disclaimer, the term of this patent is extended or adjusted under 35 U.S.C. 154(b) by 0 days.

(21) Appl. No.: 16/470,295

(22) PCT Filed: Dec. 15, 2017

(86) PCT No.: PCT/EP2017/083091
§ 371 (c)(1),
(2) Date: Jun. 17, 2019

(87) PCT Pub. No.: WO2018/109183
PCT Pub. Date: Jun. 21, 2018

(65) Prior Publication Data
US 2019/0345472 A1      Nov. 14, 2019

(30) Foreign Application Priority Data

Dec. 16, 2016  (EP) ..................................... 16306702

(51) Int. Cl.
| | | |
|---|---|---|
| *C12N 9/64* | (2006.01) | |
| *C12N 15/57* | (2006.01) | |
| *C12Q 1/37* | (2006.01) | |
| *C08J 11/10* | (2006.01) | |
| *C12N 15/52* | (2006.01) | |
| *C12N 15/74* | (2006.01) | |
| *C12P 21/02* | (2006.01) | |

(52) U.S. Cl.
CPC ........... *C12N 9/6424* (2013.01); *C08J 11/105* (2013.01); *C12N 15/52* (2013.01); *C12N 15/74* (2013.01); *C12P 21/02* (2013.01); *C08L 2201/06* (2013.01)

(58) Field of Classification Search
CPC ........ C12N 15/52; C12N 15/56; C12N 15/62; C12N 9/48; C07K 14/195
See application file for complete search history.

(56) References Cited

U.S. PATENT DOCUMENTS

2018/0142097 A1    5/2018  Guemard et al.

FOREIGN PATENT DOCUMENTS

WO    WO 2016/198652    12/2016

OTHER PUBLICATIONS

Munro, G. K. L. et al. "A gene encoding a thermophilic alkaline serine proteinase from *Thermus* sp. strain Rt41A and its expression in *Escherichia coli*" *Microbiology*, 1995, pp. 1731-1738, vol. 141.
Oda, Y. et al. "Degradation of Polylactide by Commercial Proteases" *Journal of Polymers and the Environment*, 2000, pp. 29-32, vol. 8. No. 1.
Database Protein [Online] Accession No. WP_027892186, Jun. 12, 2014, pp. 1-2, XP-002769042.
Database Protein [Online] Accession No. WP_026234785, Jun. 8, 2014, pp. 1-2, XP-002769043.
Database UniProt [Online] Accession No. P80146, Dec. 1, 1992, pp. 1-2, XP-002777996.
Written Opinion in International Application No. PCT/EP2017/083091, Feb. 23, 2018, pp. 1-7.

*Primary Examiner* — Maryam Monshipouri
(74) *Attorney, Agent, or Firm* — Saliwanchik, Lloyd & Eisenschenk

(57) ABSTRACT

The present invention relates to novel proteases, more particularly to protease variants having improved activity compared to the protease of SEQ ID NO:1 and the uses thereof for degrading polyester containing material, such as plastic products. The proteases of the invention are particularly suited to degrade polylactic acid, and material containing polylactic acid.

20 Claims, No Drawings
Specification includes a Sequence Listing.

PLASTIC DEGRADING PROTEASES

CROSS-REFERENCE TO RELATED APPLICATION

This application is the U.S. national stage application of International Patent Application No. PCT/EP2017/083091, filed Dec. 15, 2017.

The Sequence Listing for this application is labeled "Seq-List.txt" which was created on Jun. 11, 2019 and is 14 KB. The entire content of the sequence listing is incorporated herein by reference in its entirety.

The present invention relates to novel proteases, more particularly to proteases having improved activity compared to a parent protease and the uses thereof for degrading polyester containing material, such as plastic products. The proteases of the invention are particularly suited to degrade polylactic acid, and polylactic acid containing material.

BACKGROUND

Proteases are able to catalyze the hydrolysis of a variety of polymers, including polyesters. In this context, proteases have shown promising effects in a number of industrial applications, including as detergents for dishwashing and laundry applications, as degrading enzymes for processing biomass and food, as biocatalysts in the detoxification of environmental pollutants or for the treatment of polyester fabrics in the textile industry. Likewise, the use of proteases as degrading enzymes for hydrolyzing polylactic acid (PLA) is of particular interest. Indeed, PLA is a bio-based polymer that is used in a large number of technical fields, such as flexible and rigid packaging, bags, mulching films, as well as in the manufacture of clothes and carpets. Accordingly, PLA accumulation in landfills becomes an increasing ecological problem.

Among proteases, serine proteases (EC 3.4.21), are enzymes that cleave peptide amide bonds in proteins, in which serine serves as the nucleophilic amino acid in the enzyme active site. Serine proteases are found ubiquitously in both eukaryotes and prokaryotes. Numerous bacterial serine proteases have been identified initially in *Bacillus* and more recently in other mesophilic hosts. However, an increasing number of serine proteases have been isolated from thermophilic and hyperthermophilic bacteria. As an example, aqualysin I, from *Thermus aquatic* YT-1, has been cloned, sequenced and expressed in *Escherichia coli*.

Biological degradation, and more particularly enzymatic degradation, is considered as an interesting solution to decrease plastic waste accumulation. Indeed, enzymes are able to accelerate hydrolysis of polyester containing material, and more particularly of plastic products, even down to the monomer level. Furthermore, the hydrolysate (i.e., monomers and oligomers) can be recycled as material for the synthesis of new polymers. Recently, new plastic materials have been developed that integrate biological entities suitable for degrading at least one polymer of the plastic material, leading to the production of biodegradable plastic products. As an example, plastic products made of PLA and including proteases have been produced. Such biodegradable plastics may at least partially solve the problem of plastic build-up in landfill sites and natural habitats.

In this context, several proteases have been identified as candidate degrading enzymes. For instance, a protease of *Micromonospora* sp. (WO 2016/146540) has been described for its capacity to degrade polyester, and more particularly polylactic acid.

However, there is still a need for proteases with improved activity and/or improved stability at high temperatures to allow a degrading process with higher efficiency, and thereby enhancing the competitiveness of biodegradable plastic production processes, biological polyester degrading processes and/or biological recycling processes.

SUMMARY OF THE INVENTION

The present invention provides new proteases, which are variant of a parent, or wild-type protease, that may exhibit increased polyester degrading activity compared to said wild-type protease. More particularly, the present invention provides variants of a parent protease having the amino acid sequence as set forth in SEQ ID No 1, which corresponds to the amino acids 133 to 410 of the amino acid sequence referenced P80146 in UniProtKB and which corresponds to the amino acid sequence of the mature protease described in Munro et al, 1995 July, Microbiology, 141 (Pt 7):1731-8 (alkaline serine proteinase from *Thermus* sp. strain Rt41A) and described in Munro et al, 1995 as exhibiting a stability at 70° C. for more than 24 hours. Both the wild-type protease and the variants are considered as subtilisin-like proteases. The proteases of the invention are particularly useful in processes for degrading plastic material and product, such as plastic material and product containing polylactic acid (PLA). Therefore, the present invention further provides process for degrading plastic material and product containing polylactic acid (PLA) using a protease having at least 75%, 80%, 85%, 90%, 95%, 99%, 100% identity with the amino acid sequence as set forth in SEQ ID No 1 and possibly one or more substitution on specific amino acid as compared to SEQ ID No 1.

In this regard, it is an object of the invention to provide a protease variant which (i) has at least 80%, 85%, 90%, 95% or 99% identity to the full length amino acid sequence set forth in SEQ ID No 1, and (ii) has at least one substitution at a position selected from N102, S104, S106, N107, G132, G134, D160, or Y167, wherein the positions are numbered by reference to the amino acid sequence set forth in SEQ ID No 1. Advantageously, said protease variants exhibit polyester degrading activity, and preferably an increased polyester degrading activity compared to the protease of SEQ ID No 1.

In a particular embodiment, the protease comprises at least one substitution at the position S104.

According to a particular embodiment, the protease may comprise at least one combination of substitutions selected from the group consisting of S104L+N107I, S104L+Y167R, D160E+Y167R, N102S+D160E+Y167R, S106T+D160E+Y167R, N107T+D160E+Y167R, N102S+N107T+D160E+Y167R N102S+S106T+N107T+Y167R, N102F+S104L+S106T+N107I, N102F+S104L+D160E+Y167R, N102F+S104L+N107I+D160E+Y167R, N102S+S106T+N107T+D160E+Y167R, N102F+S104L+S106T+N107I+Y167R, N102F+S104L+S106T+N107I+G132I, N102F+S106T+N107T+D160E+Y167R, N102F+S104L+S106T+N107I+D160E+Y167R, N102F+S104L+S106T+N107I+G132I+Y167R, and N102F+S104L+S106T+N107I+G132I+D160E+Y167R, wherein the positions are numbered by reference to the amino acid sequence set forth in SEQ ID No 1.

It is another object of the invention to provide a nucleic acid encoding a protease of the invention. The present invention also relates to an expression cassette or an expression vector comprising said nucleic acid, and to a host cell comprising said nucleic acid, expression cassette or vector.

It is a further object of the invention to provide a method of producing a protease of the invention comprising:
(a) culturing a host cell according to the invention under conditions suitable to express a nucleic acid encoding a protease; and optionally
(b) recovering said protease from the cell culture.

The present invention also relates to a method of degrading a plastic product containing at least one polyester, preferably PLA, comprising:
(a) contacting the plastic product with a protease or host cell according to the invention, thereby degrading the plastic product; and optionally
(b) recovering monomers and/or oligomers, preferably monomers and/or oligomers of lactic acid (LA).

The present invention also relates to a polyester containing material comprising a protease or host cell according to the invention. The present invention relates more preferably to a polylactic acid (PLA) containing material comprising a protease or host cell according to the invention. The invention also provides a process for producing such polyester containing material comprising a step of mixing a polyester, preferably PLA, and a protease or host cell according to the invention, wherein the mixing step is performed at a temperature at which the polyester is in a partially or totally molten state, preferably during an extrusion process.

It is a further object of the present invention to provide a polyester containing material, more preferably a PLA containing material, comprising a protease having the amino acid sequence as set forth in SEQ ID No 1. The invention also provides a process for producing such polyester containing material comprising a step of mixing a polyester, preferably PLA, and a protease having the amino acid sequence as set forth in SEQ ID No 1, wherein the mixing step is performed at a temperature at which the polyester is in a partially or totally molten state, preferably during an extrusion process.

The present invention further relates to the use of a variant of protease as described above and/or of a protease having the amino acid sequence as set forth in SEQ ID No 1 for degrading a polyester containing material, more preferably a PLA containing material.

DETAILED DESCRIPTION OF THE INVENTION

Definitions

The present disclosure will be best understood by reference to the following definitions.

Herein, the terms "peptide", "polypeptide", "protein", "enzyme" refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

The term "protease" or "proteinase" refers to an enzyme which belongs to a class of hydrolases classified as EC 3.4 according to Enzyme Nomenclature that catalyzes the hydrolysis of peptide bonds in a peptide or a protein in order to produce shorter peptides. The term "serine protease" refers to the proteases classified as EC 3.4.21 according to the nomenclature of the Enzyme Commission.

The terms "wild-type protein" or "parent protein" are used interchangeably and refer to the non-mutated version of a polypeptide as it appears naturally. In the present case, the parent protease refers to the protease having the amino acid sequence as set forth in SEQ ID No 1.

Accordingly, the terms "mutant" and "variant" may be used interchangeably to refer to polypeptides derived from SEQ ID No 1 and comprising a modification or an alteration, i.e., a substitution, insertion, and/or deletion, at one or more (e.g., several) positions and having preferably a polyester degrading activity. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction.

The term "modification" or "alteration" as used herein in relation to a position or amino acid means that the amino acid in the particular position has been modified compared to the amino acid of the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: Y167R denotes that amino acid residue Tyrosine (Y) at position 167 of the parent sequence is changed to an Arginine (R). Y167V/I/M denotes that amino acid residue Tyrosine (Y) at position 167 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

The term "deletion", used in relation to an amino acid, means that the amino acid has been removed or is absent.

The term "insertion" means that one or more amino acids have been added.

Unless otherwise specified, the positions disclosed in the present application are numbered by reference to the amino acid sequence set forth in SEQ ID No 1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as (see Worldwide Website: blast.ncbi.nlm.nih.gov) or (see Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

The term "recombinant" refers to a nucleic acid construct, a vector, a polypeptide or a cell produced by genetic engineering.

The term "expression", as used herein, refers to any step involved in the production of a polypeptide including, but not being limited to, transcription, post-transcriptional modification, translation, post-translational modification, and secretion.

The term "expression cassette" denotes a nucleic acid construct comprising a coding region, i.e. a nucleic acid of the invention, and a regulatory region, i.e. comprising one or more control sequences, operably linked.

As used herein, the term "expression vector" means a DNA or RNA molecule that comprises an expression cassette of the invention. Preferably, the expression vector is a linear or circular double stranded DNA molecule.

A "polymer" refers to a chemical compound or mixture of compounds whose structure is constituted of multiple monomers (repeat units) linked by covalent chemical bonds. Within the context of the invention, the term polymer includes natural or synthetic polymers, constituted of a single type of repeat unit (i.e., homopolymers) or of a mixture of different repeat units (i.e., copolymers or heteropolymers). According to the invention, "oligomers" refer to molecules containing from 2 to about 20 monomers.

In the context of the invention, a "polyester containing material" or "polyester containing product" refers to a product, such as plastic product, comprising at least one polyester in crystalline, semi-crystalline or totally amorphous form. In a particular embodiment, the polyester containing material refers to any item made from at least one plastic material, such as plastic sheet, tube, rod, profile, shape, film, massive block, fiber, textiles, etc., which contains at least one polyester, and possibly other substances or additives, such as plasticizers, mineral or organic fillers. In another particular embodiment, the polyester containing material refers to textile or fabrics comprising at least one polyester containing fiber. In another particular embodiment, the polyester containing material refers to a plastic compound, or plastic formulation, in a molten or solid state, suitable for making a plastic product.

In the present description, "polyesters" encompass polylactic acid (PLA), polyethylene terephthalate (PET), polytrimethylene terephthalate (PTT), polybutylene terephthalate (PBT), polyethylene isosorbide terephthalate (PEIT), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these polymers.

Novel Proteases

By working on development of novel proteases having improved polyester-degrading activity as compared to enzymes currently available, the inventors have discovered that a serine protease having the amino acid sequence of SEQ ID No 1 and exhibiting a stability at 70° C. for more than 24 hours (Munro et al, 1995), interestingly also exhibits a polyester-degrading activity. The inventors have further worked on this enzyme and have developed particular variants of this enzyme that exhibit an improved polyester-degrading activity as compared to this parent protein. More particularly, the inventors have designed novel enzymes having superior properties for use in industrial processes. With the aim to improve the activity of proteases in conditions at which industrial production of degradable plastic products can be performed and/or environmental degradation of plastic products can be obtained, the inventors have developed novel proteases derived from the protease of SEQ ID No 1 that show higher activity compared to this parent protease. The proteases of the invention are particularly suited to degrade plastic product containing PLA. The proteases of the invention advantageously exhibit an increased specific degrading activity on a polyester, and more particularly on PLA, compared to the protease of SEQ ID No 1. Interestingly, the inventors have identified specific amino acid residues, which are intended to be in contact with a polyester substrate in the structure of the protein that may be advantageously modified to promote the contact of the polyester substrate with the protein and thereby increasing the adsorption of the enzyme on this polyester and/or the degrading activity of the protein.

Within the context of the invention, the term "increased degrading activity" indicates an increased ability of the enzyme to degrade a plastic product or material, more particularly a polyester containing plastic product or material, even more particularly a PLA containing plastic product or material, as compared to the protease of SEQ ID No 1. Such an increase is typically of about 5%, 10%, 20%, 30%, 40%, 50%, 100%, 200%, 300%, 400%, 500% or more in comparison to the parent protease.

The degrading activity of a protein may be evaluated by the one skilled in the art, according to methods known per se in the art. For instance, the activity can be assessed by the measurement of the specific protease activity rate, the measurement of the hydrolysis of pNA (N-succinyl-Ala-Ala-Ala-p-nitroanilide), the measurement of the specific polyester's depolymerization activity rate, the measurement of the rate to degrade a solid polyester compound dispersed in an agar plate, the measurement of the decrease of the turbidity of an emulsion containing a polyester, or the measurement of the specific polyester's depolymerization activity rate in reactor.

Within the context of the invention, the term "specific degrading activity" for a targeted polyester designates the initial rate of monomers and/or oligomers, in mg, released per hour and per mg of enzyme under suitable conditions of temperature, pH and buffer, when contacting a plastic product containing said targeted polyester with a protease according to the invention. As an example, the specific degrading activity for PLA corresponds to the mg of lactic acid and dimer of lactic acid produced per hour and per mg of enzyme, or to the μmol of PLA hydrolyzed/min and per mg of enzyme, as determined in the linear part of the hydrolysis curve.

According to an embodiment of the invention, the protease is a variant of the protease of SEQ ID No 1, which has at least 75%, 80%, 85%, 90%, 95% or 99% identity to the full length amino acid sequence set forth in SEQ ID No 1, and which has at least one substitution at a position selected from N102, S104, S106, N107, G132, G134, or Y167, wherein the positions are numbered by reference to the amino acid sequence set forth in SEQ ID No 1. In a particular embodiment, the protease variant further comprises an additional substitution at position D160.

According to another embodiment, the protease is a variant of the protease of SEQ ID No 1, which has at least 80%, 85%, 90%, 95% or 99% identity to the full length amino acid sequence set forth in SEQ ID No 1, and which has at least one substitution at a position selected from N102, S104, S106, N107, G132, G134, D160, or Y167, wherein the positions are numbered by reference to the amino acid sequence set forth in SEQ ID No 1.

According to the invention, the targeted amino acid(s) may be replaced by any one of the other amino acids selected from standard naturally-occurring amino acid residues, rare naturally occurring amino acid residues and non-naturally occurring amino acid residue. Preferably, the targeted amino acid(s) may be replaced by any one of the 19 other amino acids. In a particular embodiment, the protease variant comprises a single substitution as compared to SEQ ID No 1, at a position selected from N102, S104, S106, N107, G132, G134, D160, and Y167. Preferably, the protease variant comprises a single substitution selected from N102S/F, S104L, S106T, N107T/I, G132I, G134K, D160E, and Y167R, more preferably selected from N102F, S104L, N107I, G132I, G134K, D160E and Y167R, even more preferably selected from S104L and Y167R.

In another particular embodiment, the protease variant comprises more than one substitution as compared to SEQ ID No 1, and at least one substitution is at a position selected from N102, S104, S106, N107, G132, G134, D160, and Y167, preferably at position selected from Y167, S106 and S104.

Advantageously, the protease variant comprises at least one substitution selected from N102S/F, S104L, S106T, N107T/I, G132I, G134K, D160E and Y167R, preferably selected from Y167R, N102F, S104L, S106T and N107I, more preferably selected from Y167R, S106T and S104L.

In a particular embodiment, the protease variant comprises at least two substitutions at positions selected from N102, S104, S106, N107, G132, G134, D160, and Y167. In a particular embodiment, the protease variant comprises at least two substitutions selected from N102S/F, S104L, S106T, N107T/I, G132I, G134K, D160E, and Y167R.

According to a particular embodiment, the variant comprises at least the combination of two substitutions selected from D160E+Y167R; N102S+Y167R; S106T+Y167R; G134K+Y167R; S104L+G134K; N107T+Y167R; S104L+Y167R; S104L+N107I, preferably D160E+Y167R, S104L+N107I and S104L+Y167R.

In a particular embodiment, the protease variant comprises at least three substitutions at positions selected from N102, S104, S106, N107, G132, G134, D160, and Y167. In a particular embodiment, the variant comprises at least the combination of three substitutions selected from N102S+S106T+Y167R; N102S+N107T+Y167R; N102S+D160E+Y167R; S106T+N107T+Y167R; S106T+D160E+Y167R; N107T+D160E+Y167R N102F+S104L+Y167R; N102F+S104L+N107I; S104L+G134K+Y167R; G134K+D160E+Y167R; S104L+N107I+G134K; N102F+N107I+Y167R; S104L+N107I+Y167R and S104L+G132I+Y167R.

According to a particular embodiment, the variant comprises at least the combination of substitutions selected from N102S+S106T+N107T+Y167R, N102S+S106T+D160E+Y167R, N102S+N107T+D160E+Y167R, S106T+N107T+D160E+Y167R, N102F+S104L+N107I+G134K; S104L+N107I+G134K+Y167R; N102F+S104L+D160E+Y167R and N102F+S104L+S106T+N107I, preferably N102F+S104L+S106T+N107I and N102F+S104L+D160E+Y167R, more preferably N102F+S104L+S106T+N107I.

According to a particular embodiment, the variant comprises at least the combination of substitutions selected from N102S+S106T+N107T+D160E+Y167R, N102F+S106T+N107T+D160E+Y167R, N102F+S104L+N107I+D160E+Y167R, N102F+S104L+N107I+G134K+Y167R, N102F+S104L+S106T+N107I+G134K, S104L+S106T+N107I+G134K, S104L+S106T+N107I+G134K+Y167R, N102F+S104L+S106T+N107I+Y167R and N102F+S104L+S106T+N107I+G132I, preferably N102F+S104L+S106T+N107I+Y167R or N102F+S104L+S106T+N107I+G132I.

According to a particular embodiment, the variant comprises at least the combination of substitutions selected from N102F+S104L+S106T+N107I+D160E+Y167R; N102F+S104L+S106T+N107I+G134K+Y167R or N102F+S104L+S106T+N107I+G132I+Y167R, preferably N102F+S104L+S106T+N107I+D160E+Y167R.

According to a particular embodiment, the variant comprises at least the combination of substitutions N102F+S104L+S106T+N107I+G132I+D160E+Y167R or N102F+S104L+S106T+N107I+G134K+D160E+Y167R, preferably N102F+S104L+S106T+N107I+G132I+D160E+Y167R.

According to a particular embodiment, the variant comprises at least the combination of substitutions N102F+S104L+S106T+N107I+G132I+G134K+D160E+Y167R.

Advantageously, the protease variant and/or the parent protease comprises at the N-terminal end an amino acid sequence acting as a "propeptide", which is at least partially responsible for the 3D folding and the maturation of the protease.

Particularly, the protease variant and/or the parent protease comprises at the N-terminal end an amino acid sequence which has at least 75%, 80%, 85%, 90%, 95%, 99% or 100% identity to the full length amino acid sequence set forth in SEQ ID No 42.

According to a particular embodiment, the protease variant and/or the parent protease comprises at the N-terminal end an amino acid sequence which has at least 75%, 80%, 85%, 90%, 95%, or 99% identity to the full length amino acid sequence set forth in SEQ ID No 42, and has at least one amino acid substitution at a position selected from R24, Y75, D106, Q107, E108, V109, R110, A111, and F112, wherein the positions are numbered by reference to the amino acid sequence set forth in SEQ ID No 42. According to the invention, the targeted amino acid(s) may be replaced by any one of the other amino acids selected from standard naturally-occurring amino acid residues, rare naturally occurring amino acid residues and non-naturally occurring amino acid residue. Preferably, the targeted amino acid(s) may be replaced by any one of the 19 other amino acids.

Polyester Degrading Activity of the Variant

It is an object of the invention to provide new enzymes having a protease activity.

In a particular embodiment, the protease variant of the invention has a polyester degrading activity, preferably a polylactic acid degrading activity. Interestingly, the parent protease, having the amino acid sequence as set forth in SEQ ID No 1 also has a polyester degrading activity, preferably a polylactic acid degrading activity. Preferably, the protease variant of the invention exhibits an increased a polyester degrading activity compared to the protease of SEQ ID No 1.

Advantageously, the protease variant and/or the parent protease of the invention exhibits a polyester degrading activity at least in a range of temperatures from 10° C. to 90° C., preferably from 40° C. to 80° C., more preferably from 60° C. to 80° C., even more preferably from 70° C. to 80° C., even more preferably at 75° C. In another particular embodiment, the protease variant and/or the parent protease of the invention exhibits a polyester degrading activity from 20° C. to 80° C., preferably from 30° C. to 70° C., more preferably from 40° C. to 60° C., even more preferably from 40° C. to 50° C., preferably at 45° C. In a particular embodiment, the polyester degrading activity is still measurable at a temperature between 40° C. and 80° C., preferably between 40° C. and 60° C., even more preferably at 45° C. In another particular embodiment, the polyester degrading activity is still measurable at a temperature between 10° C. and 30° C., preferably between 15° C. and 28° C., corresponding to the mean temperature in the natural environment.

In a particular embodiment, the protease variant has a polyester degrading activity at 45° C. at least 5% higher than the polyester degrading activity of the protease of SEQ ID No 1, preferably at least 10%, 20%, 30%, 40%, 50%, 100%, 200%, 300%, 500% or higher.

In another particular embodiment, the protease variant of the invention has an increased polyester degrading activity, compared to the protease of SEQ ID No 1, at a temperature between 10° C. and 90° C., more preferably between 40° C. and 80° C., even more preferably between 60° C. and 80° C., even more preferably at 75° C. In a particular embodiment, the protease variant has a polyester degrading activity at 75° C. at least 5% higher than the polyester degrading activity of the protease of SEQ ID No 1, preferably at least 10%, 20%, 30%, 40%, 50%, 100%, 200%, 300%, 500% or higher.

In a particular embodiment, the protease variant of the invention has an increased polyester degrading activity, compared to the protease of SEQ ID No 1, at a temperature between 10° C. and 30° C., more preferably between 15° C. and 30° C., even more preferably between 20° C. and 30° C., even more preferably at 28° C. In a particular embodiment, the protease variant has a polyester degrading activity at 28° C. at least 5% higher than the polyester degrading activity of the protease of SEQ ID No 1, preferably at least 10%, 20%, 50%, 100%, 200%, 300%, 500% or higher.

In a particular embodiment, the protease variant of the invention exhibits a measurable polyester degrading activity at least in a range of pH from 5 to 11, preferably in a range of pH from 6 to 10, more preferably in a range of pH from 6.5 to 9, even more preferably in a range of pH from 7 to 8.

Thermostability of the Variant

Advantageously, the thermostability of the variants is not significantly impaired compared to the thermostability of the parent protease. More advantageously, the thermostability of the variants is improved compared to the thermostability of the parent protease of SEQ ID No 1. Within the context of the invention, the term "improved thermostability" indicates an increased ability of the enzyme to resist to changes in its chemical and/or physical structure at high temperatures, and more particularly at temperature between 40° C. and 90° C., as compared to the protease of SEQ ID No 1. In particular, the proteases of the present invention can have an increased half-life at a temperature between 40° C. and 90° C., as compared to the protease of SEQ ID No 1. Particularly, the proteases may exhibit a higher or equivalent melting temperature (Tm) as compared to the protease of SEQ ID No 1. Particularly, the variant of the invention shows an improved thermostability during an extrusion process, and more particularly during an extrusion process implemented at a temperature comprised between 50° C. and 250° C., preferably between 130° C. and 180° C.

The proteases of the invention may comprise one or several modifications as disclosed above.

The thermostability of a protein may be evaluated by the one skilled in the art, according to methods known per se in the art. For instance, thermostability can be assessed by measuring the residual protease activity and/or the residual polyester depolymerization activity (i.e., polyester degrading activity) of the enzyme after incubation at different temperatures. The ability to perform multiple rounds of polyester's depolymerization assays at different temperatures can also be evaluated. A rapid and qualitative test may consist on the evaluation, by halo diameter measurement, of the enzyme ability to degrade a solid polyester compound dispersed in an agar plate after incubation at different temperatures. Alternatively, or in addition, a Differential Scanning Fluorimetry (DSF) may be performed to assess the thermostability of a protein/enzyme. In the context of the invention, circular dichroism is used to quantify the change in thermal denaturation temperature of a protein and thereby to determine its melting temperature (Tm). In the context of the invention, the "melting temperature (Tm)" of a given protein corresponds to the temperature at which 50% of said protein is denatured. The Tm may be measured using circular dichroism, as exposed in the experimental part.

In a particular embodiment, the protease variant of the invention exhibits a melting temperature (Tm) above 70° C., preferably above 75° C. Interestingly, the parent protease, having the amino acid sequence as set forth in SEQ ID No 1 also exhibits a melting temperature (Tm) above 70° C., preferably above 75° C.

Nucleic Acids, Expression Cassette, Vector, Host Cell

It is a further object of the invention to provide a nucleic acid encoding a protease as defined above.

As used herein, the term "nucleic acid", "nucleic sequence," "polynucleotide", "oligonucleotide" and "nucleotide sequence" are used interchangeably and refer to a sequence of deoxyribonucleotides and/or ribonucleotides. The nucleic acids can be DNA (cDNA or gDNA), RNA, or a mixture of the two. It can be in single stranded form or in duplex form or a mixture of the two. It can be of recombinant, artificial and/or synthetic origin and it can comprise modified nucleotides, comprising for example a modified bond, a modified purine or pyrimidine base, or a modified sugar. The nucleic acids of the invention can be in isolated or purified form, and made, isolated and/or manipulated by techniques known per se in the art, e.g., cloning and expression of cDNA libraries, amplification, enzymatic synthesis or recombinant technology. The nucleic acids can also be synthesized in vitro by well-known chemical synthesis techniques, as described in, e.g., Belousov (1997) Nucleic Acids Res. 25:3440-3444.

The invention also encompasses nucleic acids which hybridize, under stringent conditions, to a nucleic acid encoding a protease as defined above. Preferably, such stringent conditions include incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

The invention also encompasses nucleic acids encoding a protease of the invention, wherein the sequence of said nucleic acids, or a portion of said sequence at least, has been engineered using optimized codon usage.

Alternatively, the nucleic acids according to the invention may be deduced from the sequence of the protease according to the invention and codon usage may be adapted according to the host cell in which the nucleic acids shall be transcribed. These steps may be carried out according to methods well known to one skilled in the art and some of which are described in the reference manual Sambrook et al. (Sambrook et al., 2001).

Nucleic acids of the invention may further comprise additional nucleotide sequences, such as regulatory regions, i.e., promoters, enhancers, silencers, terminators, signal peptides and the like that can be used to cause or regulate expression of the polypeptide in a selected host cell or system. Alternatively or in addition, nucleic acids of the invention may further comprise additional nucleotide sequences encoding fusion proteins, such as maltose binding protein (MBP) or glutathion S transferase (GST) that can be used to favor polypeptide expression and/or solubility.

The present invention further relates to an expression cassette comprising a nucleic acid according to the invention operably linked to one or more control sequences that direct the expression of said nucleic acid in a suitable host cell. Typically, the expression cassette comprises, or consists of, a nucleic acid according to the invention operably linked to a control sequence such as transcriptional promoter and/or transcription terminator. The control sequence may include a promoter that is recognized by a host cell or an in vitro expression system for expression of a nucleic acid encoding a protease of the present invention. The promoter contains transcriptional control sequences that mediate the expression of the enzyme. The promoter may be any polynucleotide that shows transcriptional activity in the host cell including mutant, truncated, and hybrid promoters, and may be obtained from genes encoding extracellular or intracellular polypeptides either homologous or heterologous to the host cell. The control sequence may also be a transcription terminator, which is recognized by a host cell to terminate transcription. The terminator is operably linked to the 3'-terminus of the nucleic acid encoding the protease. Any terminator that is functional in the host cell may be used in the present invention. Typically, the expression cassette comprises, or consists of, a nucleic acid according to the invention operably linked to a transcriptional promoter and a transcription terminator.

The invention also relates to a vector comprising a nucleic acid or an expression cassette as defined above.

The term "vector" refers to DNA molecule used as a vehicle to transfer recombinant genetic material into a host cell. The major types of vectors are plasmids, bacteriophages, viruses, fosmids, cosmids, and artificial chromosomes. The vector itself is generally a DNA sequence that consists of an insert (a heterologous nucleic acid sequence, transgene) and a larger sequence that serves as the "backbone" of the vector. The purpose of a vector which transfers genetic information to the host is typically to isolate, multiply, or express the insert in the target cell. Vectors called expression vectors (expression constructs) are specifically adapted for the expression of the heterologous sequences in the target cell, and generally have a promoter sequence that drives expression of the heterologous sequences encoding a polypeptide.

Generally, the regulatory elements that are present in an expression vector include a transcriptional promoter, a ribosome binding site, a terminator, and optionally present operator. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. Expression vectors providing suitable levels of polypeptide expression in different hosts are well known in the art. The choice of the vector will typically depend on the compatibility of the vector with the host cell into which the vector is to be introduced.

It is another object of the invention to provide a host cell comprising a nucleic acid, an expression cassette or a vector as described above. The present invention thus relates to the use of a nucleic acid, expression cassette or vector according to the invention to transform, transfect or transduce a host cell. The choice of the vector will typically depend on the compatibility of the vector with the host cell into which it must be introduced.

According to the invention, the host cell may be transformed, transfected or transduced in a transient or stable manner. The expression cassette or vector of the invention is introduced into a host cell so that the cassette or vector is maintained as a chromosomal integrant or as a self-replicating extra-chromosomal vector. The term "host cell" also encompasses any progeny of a parent host cell that is not identical to the parent host cell due to mutations that occur during replication. The host cell may be any cell useful in the production of a variant of the present invention, e.g., a prokaryote or a eukaryote. The prokaryotic host cell may be any Gram-positive or Gram-negative bacterium. The host cell may also be a eukaryotic cell, such as a yeast, fungal, mammalian, insect or plant cell. In a particular embodiment, the host cell is selected from the group of *Escherichia coli, Bacillus, Streptomyces, Trichoderma, Aspergillus, Saccharomyces, Pichia, Thermus* or *Yarrowia*.

The nucleic acid, expression cassette or expression vector according to the invention may be introduced into the host cell by any method known by the skilled person, such as electroporation, conjugation, transduction, competent cell transformation, protoplast transformation, protoplast fusion, biolistic "gene gun" transformation, PEG-mediated transformation, lipid-assisted transformation or transfection, chemically mediated transfection, lithium acetate-mediated transformation, liposome-mediated transformation.

Optionally, more than one copy of a nucleic acid, cassette or vector of the present invention may be inserted into a host cell to increase production of the variant.

In a particular embodiment, the host cell is a recombinant microorganism. The invention indeed allows the engineering of microorganisms with improved capacity to degrade polyester containing material. For instance, the sequence of the invention may be used to complement a wild type strain of a fungus or bacterium already known as able to degrade polyester, in order to improve and/or increase the strain capacity.

Production of Protease Variants

It is another object of the invention to provide a method of producing the protease variant of the invention, comprising expressing a nucleic acid encoding the protease and optionally recovering the protease.

In particular, the present invention relates to in vitro methods of producing a protease of the present invention comprising (a) contacting a nucleic acid, cassette or vector of the invention with an in vitro expression system; and (b) recovering the protease produced. In vitro expression systems are well-known by the person skilled in the art and are commercially available.

Preferably, the method of production comprises:

(a) culturing a host cell that comprises a nucleic acid encoding a protease of the invention under conditions suitable to express the nucleic acid; and optionally (b) recovering said protease from the cell culture.

Advantageously, the host cell is a recombinant *Bacillus*, recombinant *E. coli*, recombinant *Aspergillus*, recombinant *Trichoderma*, recombinant *Streptomyces*, recombinant *Saccharomyces*, recombinant *Pichia*, recombinant *Thermus* or recombinant *Yarrowia*. Preferably, the host cell is a recombinant *Bacillus*.

The host cells are cultivated in a nutrient medium suitable for production of polypeptides, using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the enzyme to be expressed and/or isolated. The cultivation takes place in a suitable nutrient medium, from commercial suppliers or prepared according to published compositions (e.g., in catalogues of the American Type Culture Collection) or any other culture medium suitable for cell growth.

If the protease is excreted into the nutrient medium, the protease can be recovered directly from the culture supernatant. Conversely, the protease can be recovered from cell lysates or after permeabilisation. The protease may be recovered using any method known in the art. For example, the protease may be recovered from the nutrient medium by conventional procedures including, but not limited to, collection, centrifugation, filtration, extraction, spray-drying, evaporation, or precipitation. Optionally, the protease may be partially or totally purified by a variety of procedures known in the art including, but not limited to, thermal chock, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction to obtain substantially pure polypeptides.

The protease may be used as such, in purified form, either alone or in combination with additional enzymes, to catalyze enzymatic reactions involved in the degradation and/or recycling of a polyester containing material, such as plastic products containing polyester. The protease may be in soluble form, or on solid phase. In particular, it may be bound to cell membranes or lipid vesicles, or to synthetic supports such as glass, plastic, polymers, filter, membranes, e.g., in the form of beads, columns, plates and the like.

Composition

It is a further object of the invention to provide a composition comprising a protease or a host cell of the invention.

In the context of the invention, the term "composition" encompasses any kind of compositions comprising a protease of the invention. In a particular embodiment, the protease is in isolated or at least partially purified form.

The composition may be liquid or dry, for instance in the form of a powder. In some embodiments, the composition is a lyophilisate. For instance, the composition may comprise the protease and/or host cells encoding the protease of the invention or an extract thereof containing said protease, and optionally excipients and/or reagents etc. Appropriate excipients encompass buffers commonly used in biochemistry, agents for adjusting pH, preservatives such as sodium benzoate, sodium sorbate or sodium ascorbate, conservatives, protective or stabilizing agents such as starch, dextrin, arabic gum, salts, sugars e.g. sorbitol, trehalose or lactose, glycerol, polyethyleneglycol, polyethene glycol, polypropylene glycol, propylene glycol, divalent ions such as calcium, sequestering agent such as EDTA, reducing agents, amino acids, a carrier such as a solvent or an aqueous solution, and the like. The composition of the invention may be obtained by mixing the protease with one or several excipients.

The composition of the invention may comprise from 0.1% to 99.9%, preferably from 0.1% to 50%, more preferably from 0.1% to 30%, even more preferably from 0.1% to 5% by weight of the protease of the invention and from 0.1% to 99.9%, preferably from 50% to 99.9%, more preferably from 70% to 99.9%, even more preferably from 95% to 99.9% by weight of excipient(s). A preferred composition comprises between 0.1 and 5% by weight of the protease of the invention.

In a particular embodiment, the composition may further comprise additional polypeptide(s) exhibiting an enzymatic activity. The amounts of protease of the invention will be easily adapted by those skilled in the art depending e.g., on the nature of the polyester containing material to degrade and/or the additional enzymes/polypeptides contained in the composition.

In a particular embodiment, the protease of the invention is solubilized in an aqueous medium together with one or several excipients, especially excipients which are able to stabilize or protect the polypeptide from degradation. For instance, the protease of the invention may be solubilized in water, eventually with additional components, such as glycerol, sorbitol, dextrin, starch, glycol such as propanediol, salt, etc. The resulting mixture may then be dried so as to obtain a powder. Methods for drying such mixture are well known to the one skilled in the art and include, without limitation, lyophilisation, freeze-drying, spray-drying, supercritical drying, down-draught evaporation, thin-layer evaporation, centrifugal evaporation, conveyer drying, fluidized bed drying, drum drying or any combination thereof.

In a further particular embodiment, the composition of the invention comprises at least one host cell expressing a protease of the invention, or an extract thereof. An "extract of a cell" designates any fraction obtained from a cell, such as cell supernatant, cell debris, cell walls, DNA extract, enzymes or enzyme preparation or any preparation derived from cells by chemical, physical and/or enzymatic treatment, which is essentially free of living cells. Preferred extracts are enzymatically-active extracts. The composition of the invention may comprise one or several host cells of the invention or extract thereof containing the protease of the invention, and optionally one or several additional cells.

In a particular embodiment, the composition consists or comprises a lyophilized culture medium of a recombinant microorganism expressing and/or excreting a protease of the invention. In a particular embodiment, the powder comprises the protease of the invention and a stabilizing/solubilizing amount of glycerol, sorbitol or dextrin, such as maltodextrine and/or cyclodextrine, starch, arabic gum, glycol such as propanediol, and/or salt.

Uses of the Proteases

The inventors have also surprisingly discovered that the parent protein also has a polyester degradation activity, specifically a polylactic acid degradation activity.

Thus, it is another object of the invention to provide methods using a polypeptide comprising an amino acid sequence having at least 75%, 80%, 85%, 90%, 95%, 99% or 100% identity to the full length amino acid sequence set forth in SEQ ID No 1, and having a polyester degrading activity for degrading in aerobic or anaerobic conditions and/or recycling polyester containing material, as plastic products made of or containing polyesters and/or producing biodegradable plastic products containing polyester. Such protease is particularly useful for producing biodegradable plastic products containing PLA and/or for degrading a plastic product comprising PLA.

It is a further object of the invention to provide methods using a protease variant of the invention for degrading in aerobic or anaerobic conditions and/or recycling polyester containing material, as plastic products made of or containing polyesters and/or producing biodegradable plastic products containing polyester. The variants of protease of the invention are particularly useful for producing biodegradable plastic products containing PLA and/or for degrading a plastic product comprising PLA.

It is therefore an object of the invention to use a protease of the invention, or corresponding host cell or extract thereof containing such protease, or composition, or a protease comprising an amino acid sequence having at least 75%, 80%, 85%, 90%, 95%, 99% or 100% identity to the full length amino acid sequence set forth in SEQ ID No 1, and having a polyester degrading activity for the enzymatic degradation of a polyester containing material, such as a PLA containing material.

It is another object of the invention to provide a method for degrading a plastic product containing at least one polyester, wherein the plastic product is contacted with a protease or host cell or composition of the invention, or a protease comprising an amino acid sequence having at least 75%, 80%, 85%, 90%, 95%, 99% or 100% identity to the full length amino acid sequence set forth in SEQ ID No 1, and having a polyester degrading activity, thereby degrading the plastic product. Advantageously, polyester(s) of the polyester containing material is (are) depolymerized up to monomers and/or oligomers. In an embodiment of the method of degradation, at least one polyester is degraded to yield repolymerizable monomers and/or oligomers, which are advantageously retrieved in order to be used. In a preferred embodiment of the method of degradation, at least PLA is degraded to yield repolymerizable monomers and/or oligomers of lactic acid (LA), which are advantageously retrieved in order to be used for instance to produce new polymers of PLA.

In an embodiment, polyester(s) of the polyester containing material is (are) fully degraded.

In a particular embodiment, the plastic product comprises at least one polyester selected from polylactic acid (PLA), polytrimethylene terephthalate (PTT), polybutylene terephthalate (PBT), polyethylene isosorbide terephthalate (PEIT), polyethylene terephthalate (PET), polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these materials, preferably polylactic acid.

In a particular embodiment, a plastic product containing PLA is contacting with a protease of the invention or a protease comprising an amino acid sequence having at least 75%, 80%, 85%, 90%, 95%, 99% or 100% identity to the full length amino acid sequence set forth in SEQ ID No 1, and having a polyester degrading activity and PLA is degraded to monomers and/or oligomers of lactic acid. In a preferred embodiment, monomers and/or oligomers of lactic acid are recovered for recycling, polymerizing PLA or methanisation for instance.

The invention also relates to a method of producing monomers and/or oligomers from a polyester containing material, comprising exposing a polyester containing material to a protease of the invention, or corresponding host cell or extract thereof, or composition, or a protease comprising an amino acid sequence having at least 75%, 80%, 85%, 90%, 95%, 99% or 100% identity to the full length amino acid sequence set forth in SEQ ID No 1, and having a polyester degrading activity and optionally recovering monomers and/or oligomers. The method of the invention is particularly useful for producing monomers such as lactic acid from plastic product containing PLA.

The time required for degrading a polyester containing material may vary depending on the polyester containing material itself (i.e., nature and origin of the plastic product, its composition, shape etc.), the type and amount of protease used, as well as various process parameters (i.e., temperature, pH, additional agents, etc.). One skilled in the art may easily adapt the process parameters to the polyester containing material.

Advantageously, the degrading process is implemented at a temperature comprised between 20° C. and 90° C., preferably between 40° C. and 80° C., more preferably between 60° C. and 80° C., more preferably between 70° C. and 80° C., even more preferably at 75° C. More generally, the temperature is maintained below an inactivating temperature, which corresponds to the temperature at which the protease is inactivated and/or the recombinant microorganism does no more synthesize the protease. Preferably, the temperature is maintained below the glass transition temperature (Tg) of the polyester in the polyester containing material. In this embodiment, the degrading process is implemented at a temperature comprised between 20° C. and 80° C., preferably between 30° C. and 70° C., more preferably between 40° C. and 60° C., more preferably between 40° C. and 50° C., even more preferably at 45° C. More particularly, the process is implemented in a continuous way, at a temperature at which the protease can be used several times and/or recycled.

Advantageously, the degrading process is implemented at a pH comprised between 5 and 11, preferably at a pH between 6 and 10, more preferably at a pH between 6.5 and 9, even more preferably at a pH between 7 and 8.

In a particular embodiment, the polyester containing material may be pretreated prior to be contacted with the protease, in order to physically change its structure, so as to increase the surface of contact between the polyester and the enzyme.

Optionally, monomers and/or oligomers resulting from the depolymerization may be recovered, sequentially or continuously. A single type of monomers and/or oligomers or several different types of monomers and/or oligomers may be recovered, depending on the starting polyester containing material.

The recovered monomers and/or oligomers may be further purified, using all suitable purifying methods and conditioned in a repolymerizable form. Examples of purifying methods include stripping process, separation by aqueous solution, steam selective condensation, filtration and concentration of the medium after the bioprocess, separation, distillation, vacuum evaporation, extraction, electrodialysis, adsorption, ion exchange, precipitation, crystallization, concentration and acid addition dehydration and precipitation, nanofiltration, acid catalyst treatment, semi continuous mode distillation or continuous mode distillation, solvent extraction, evaporative concentration, evaporative crystallization, liquid/liquid extraction, hydrogenation, azeotropic distillation process, adsorption, column chromatography, simple vacuum distillation and microfiltration, combined or not.

The repolymerizable monomers and/or oligomers may then be used for instance to synthesize polyesters. Advantageously, polyesters of same nature are repolymerized. However, it is possible to mix the recovered monomers and/or oligomers with other monomers and/or oligomers, in order for instance to synthesize new copolymers. Alternatively, the recovered monomers may be used as chemical intermediates in order to produce new chemical compounds of interest.

It is a further object of the invention to provide a polyester containing material in which a protease of the invention and/or a recombinant microorganism expressing and/or excreting said protease and/or extract thereof containing such protease, and/or a composition of the invention and/or a protease comprising an amino acid sequence having at least 75%, 80%, 85%, 90%, 95%, 99% or 100% identity to the full length amino acid sequence set forth in SEQ ID No 1, and having a polyester degrading activity is/are included. In a particular embodiment, such polyester containing material may be a plastic compound, a masterbatch composition and/or a plastic product. In the context of the invention, a "masterbatch composition" refers to a concentrated mixture of selected ingredients (e.g., active agents, additives, etc.) that can be used for introducing said ingredients into plastic compound or product in order to impart desired properties thereto. Masterbatch compositions may be solid or liquid. Preferably, masterbatch compositions of the invention contain at least 10% by weight of active ingredients, more preferably of protease of the invention.

It is thus a further object of the invention to provide a plastic compound containing a protease of the invention and/or a recombinant microorganism expressing and/or excreting said protease or extract thereof containing such protease and/or a composition of the invention and/or a protease comprising an amino acid sequence having at least 75%, 80%, 85%, 90%, 95%, 99% or 100% identity to the full length amino acid sequence set forth in SEQ ID No 1, and having a polyester degrading activity, and at least one polyester. In a particular embodiment, the polyester is polylactic acid (PLA), preferably poly(L-lactic acid) (PLLA), poly(D-lactic acid) (PDLA) or poly(DL-lactic acid) (PDLLA). In a particular embodiment, the plastic compound may contain an additional polymer, preferably selected from polyesters such as PBAT, PCL, PET; polyolefins such as polyethylene, polypropylene or natural polymers such as starch, cellulose or flour; and blends/mixtures thereof. More particularly, the plastic compound may contain additional polymers selected from PBAT, flour or starch. In another particular embodiment, the polyester is preferably polycaprolactone (PCL).

It is thus a further object of the invention to provide a masterbatch composition containing a protease of the invention and/or a recombinant microorganism expressing and/or excreting said protease or extract thereof containing such protease and/or a composition of the invention and/or a protease comprising an amino acid sequence having at least 75%, 80%, 85%, 90%, 95%, 99% or 100% identity to the full length amino acid sequence set forth in SEQ ID No 1, and having a polyester degrading activity, and at least one polyester. In a particular embodiment, the polyester is polylactic acid (PLA), preferably poly(L-lactic acid) (PLLA), poly(D-lactic acid) (PDLA) or poly(DL-lactic acid) (PDLLA). In another particular embodiment, the polyester is preferably polycaprolactone (PCL).

In particular, the invention relates to a process for producing such polyester containing material (i.e., plastic compound, masterbatch composition or plastic product) comprising a step of mixing a polyester and a protease and/or recombinant microorganism of the invention or extract thereof containing such protease and/or a composition of the invention, and/or a protease comprising an amino acid sequence having at least 75%, 80%, 85%, 90%, 95%, 99% or 100% identity to the full length amino acid sequence set forth in SEQ ID No 1, that degrades said polyester, at a temperature at which the polyester is in a partially or totally molten state so that the protease/microorganisms are integrated into the very structure of the polyester containing material. In a particular embodiment, the process is an extrusion process.

For instance, the protease and/or the composition of the invention and/or a protease comprising an amino acid sequence having at least 75%, 80%, 85%, 90%, 95%, 99% or 100% identity to the full length amino acid sequence set forth in SEQ ID No 1, and having a polyester degrading activity and the polyester may be mixed at a temperature between the glass transition temperature and the melting point of the polyester. Alternatively, the protease/composition of the invention and/or a protease comprising an amino acid sequence having at least 75%, 80%, 85%, 90%, 95%, 99% or 100% identity to the full length amino acid sequence set forth in SEQ ID No 1, and having a polyester degrading activity, and the polyester may be mixed at a temperature corresponding to the melting point of said polyester, or above. In a particular embodiment, the protease/composition and/or protease comprising an amino acid sequence having at least 75%, 80%, 85%, 90%, 95%, 99% or 100% identity to the full length amino acid sequence set forth in SEQ ID No 1, and having a polyester degrading activity, and the polyester are mixed at a temperature between 40° C. and 250° C., preferably between 50° C. and 180° C. Alternatively, the polypeptide/composition and the polyester are mixed at a temperature above 40° C., preferably above 50° C., even more preferably above 60° C.

In a preferred embodiment, the polyester is selected from polylactic acid (PLA), and the protease/composition and PLA are mixed at a temperature between 60° C. and 250° C., preferably between 100° C. and 200° C., more preferably between 130° C. and 180° C., even more preferably between 140° C. and 160° C. Alternatively, the polypeptide/composition and PLA are mixed at a temperature above 80° C., preferably, above 100° C., even more preferably above 130° C., and below 180° C.

In another preferred embodiment, the polyester is selected from polycaprolactone (PCL), and the protease/composition and PCL are mixed at a temperature between 40° C. and 100° C., preferably between 50° C. and 80° C. Alternatively, the polypeptide/composition and PCL are mixed at a temperature above 40° C., preferably, above 50° C., even more preferably above 55° C., and below 80° C.

More preferably, the mixing step is performed using extrusion, twin screw extrusion, single screw extrusion, injection-molding, casting, thermoforming, rotary molding, compression, calendering, ironing, coating, stratification, expansion, pultrusion, extrusion blow-molding, extrusion-swelling, compression-granulation, water-in-oil-in-water double emulsion evaporation, 3D printing or any techniques known by person skilled in the art.

The resulting plastic compound, masterbatch composition or plastic product integrates protease/microorganism or composition of the invention embedded in the mass of the compound, masterbatch composition or plastic product.

Advantageously, such plastic compound or masterbatch composition can be used for the production of polyester containing materials and/or plastic article that will thus include the polypeptide of the invention.

In a particular embodiment, the resulting plastic compound, masterbatch composition or plastic article is a biodegradable plastic compound, masterbatch composition or plastic article complying with at least one of the relevant standards and/or labels known by the person skilled in the art, such as standard EN 13432, standard ASTM D6400, OK Biodegradation Soil (Label Vincotte), OK Biodegradation Water (Label Vincotte), OK Compost (Label Vincotte), OK Home Compost (Label Vincotte).

Advantageously, the degrading process of the polyester containing material (i.e., plastic compound, masterbatch composition or plastic product) is implemented at a temperature comprised between 10° C. and 50° C., preferably between 15° C. and 40° C., more preferably between 20° C. and 30° C., more preferably at 28° C., +/−2° C.

Alternatively, the degrading process of the polyester containing material (i.e., plastic compound, masterbatch composition or plastic product) is implemented at a temperature comprised between 50° C. and 60° C., more preferably at 55° C., +/−2° C.

Classically, a protease of the invention or a protease comprising an amino acid sequence having at least 75%, 80%, 85%, 90%, 95%, 99% or 100% identity to the full length amino acid sequence set forth in SEQ ID No 1, may be used in detergent, food, animal feed and pharmaceutical applications.

More particularly, a protease of the invention or a protease comprising an amino acid sequence having at least 75%, 80%, 85%, 90%, 95%, 99% or 100% identity to the full length amino acid sequence set forth in SEQ ID No 1, may be used as a component of a detergent composition.

Detergent compositions include, without limitation, hand or machine laundry detergent compositions, such as laundry additive composition suitable for pre-treatment of stained fabrics and rinse added fabric softener composition, detergent composition for use in general household hard surface cleaning operations, detergent compositions for hand or machine dishwashing operations.

In a particular embodiment, a protease of the invention or protease comprising an amino acid sequence having at least 75%, 80%, 85%, 90%, 95%, 99% or 100% identity to the full length amino acid sequence set forth in SEQ ID No 1, may be used as a detergent additive. The invention thus provides detergent compositions comprising a protease of the invention or protease comprising an amino acid sequence having at least 75%, 80%, 85%, 90%, 95%, 99% or 100% identity to the full length amino acid sequence set forth in SEQ ID No 1.

The present invention is also directed to methods for using a protease of the invention or protease comprising an amino acid sequence having at least 75%, 80%, 85%, 90%, 95%, 99% or 100% identity to the full length amino acid sequence set forth in SEQ ID No 1, in animal feed, as well as to feed compositions and feed additives comprising a protease of the invention or protease comprising an amino acid sequence having at least 75%, 80%, 85%, 90%, 95%, 99% or 100% identity to the full length amino acid sequence set forth in SEQ ID No 1. The terms "feed" and "feed composition" refer to any compound, preparation, mixture, or composition suitable for, or intended for intake by an animal.

In another particular embodiment, the protease of the invention or protease comprising an amino acid sequence having at least 75%, 80%, 85%, 90%, 95%, 99% or 100% identity to the full length amino acid sequence set forth in SEQ ID No 1 is used to hydrolyze proteins, and to produce hydrolysates comprising peptides. Such hydrolysates may be used as feed composition or feed additives.

The invention also relates to a method of surface hydrolysis or surface functionalization of a polyester containing material, comprising exposing a polyester containing material to a protease of the invention, or protease comprising an amino acid sequence having at least 75%, 80%, 85%, 90%, 95%, 99% or 100% identity to the full length amino acid sequence set forth in SEQ ID No 1, or corresponding recombinant cell or extract thereof, or composition. The method of the invention is particularly useful for increasing hydrophilicity, or water absorbency, of a polyester material. Such increased hydrophilicity may have particular interest in textiles production, electronics and biomedical applications.

EXAMPLES

Example 1

Construction, Expression and Purification of Proteases

—Construction

The gene coding for the parent protease from *Thermus* sp. (strain Rt41A) was cloned in the plasmid pET26b⁺ (EMD Millipore, Billerica, Mass., USA). The gene (SEQ ID No 2) encoding the parent protease of SEQ ID No 1 and its natural propeptide (SEQ ID No 42), was inserted in the plasmid pET26b⁺ in frame with sequences encoding PelB signal peptide (SEQ ID No 43: MKYLLPTAAAGLLLLAAQ-PAMA) upstream of the gene and encoding a 6×histidine tag (SEQ ID No 44: LEHHHHHH) downstream of the gene. *E. coli* One Shot® BL21 DE3 (Life technologies, Carlsbad, Calif., USA) was transformed with the constructed plasmid. The obtained strain expresses the wild-type protease with a PelB signal sequence at the N-terminal and a 6×histidine Tag at the C-terminal of the protein. QuikChange II Site-Directed Mutagenesis kit was used according to the recommendations of the supplier to construct the variants (Santa Clara, Calif., USA). The Table 1 gives forward and reverse primers used for the site-directed mutagenesis.

TABLE 1

Forward and reverse primers used for site-directed mutagenesis of the gene coding for parent protease for the production of protease variants of the invention

| | Sequences |
|---|---|
| N102S forward (SEQ ID No 3) | 5'-CTCGACTGTAGCGGTTCCGGATC-3' |
| N102S reverse (SEQ ID No 4) | 5'-GATCCGGAACCGCTACAGTCGAG-3' |
| S106T forward (SEQ ID No 5) | 5'-TCCGGAACTAACTCCTCTGTCATC-3' |
| S106T reverse (SEQ ID No 6) | 5'-GGAGTTAGTTCCGGAACCGTTACA-3' |
| N107T forward (SEQ ID No 7) | 5'-CCGGATCTACCTCCTCTGTC-3' |
| N107T reverse (SEQ ID No 8) | 5'-GACAGAGGAGGTAGATCCGG-3' |
| D160E forward (SEQ ID No 9) | 5'-GCTGGTAACGAAAACCGAGACG-3' |
| D160E reverse (SEQ ID No 10) | 5'-CGTCTCGGTTTTCGTTACCAGC-3' |
| Y167R forward (SEQ ID No 11) | 5'-CGAGACGCTTGTTTCCGCTCTCCCGCTCGAGTCAC-3' |
| Y167R reverse (SEQ ID No 12) | 5'-GAAACAAGCGTCTCGGTTGTCGTTACCAGCAGC-3' |
| D160E + Y167R forward (SEQ ID No 13) | 5'-TAACGAAAACCGAGACGCTTGTTTCCGCTCTCCCGCTC-3' |
| D160E + Y167R reverse (SEQ ID No 14) | 5'-GGGAGAGCGGAAACAAGCGTCTCGGTTTTCGTTACCAGCA-3' |
| N102S + S106T + N107T forward (SEQ ID No 15) | 5'-TGTAGCGGTTCCGGAACTACCTCCTCTGTCATC-3' |
| N102S + S106T + N107T reverse (SEQ ID No 16) | 5'-AGGAGGTAGTTCCGGAACCGCTACAGTCGAGCACT-3' |
| N102F forward (SEQ ID No 17) | 5'-GACTGTTTCGGTTCCGGATCTAAC-3' |
| N102F forward mutated (SEQ ID No 18) | 5'-GACTGTTTCGGTTCCGGAACTACC-3' |
| N102F reverse (SEQ ID No 19) | 5'-GGAACCGAAACAGTCGAGCACTC-3' |
| S104L forward (SEQ ID No 20) | 5'-AACGGTCTCGGATCTAACTCCTCT-3' |
| S104L reverse (SEQ ID No 21) | 5'-AGATCCGAGACCGTTACAGTCGAG-3' |
| N107I forward (SEQ ID No 22) | 5'-GGATCTATCTCCTCTGTCATCGCT-3' |
| N107I reverse (SEQ ID No 23) | 5'-AGAGGAGATAGATCCGGAACCGTT-3' |
| S104L + N107I forward (SEQ ID No 24) | 5'-AACGGTCTCGGATCTATCTCCTCTGTCAT-3' |
| S104L + N107I reverse (SEQ ID No 25) | 5'-AGAGGAGATAGATCCGAGACCGTTACAGT-3' |
| N102F + S104L forward (SEQ ID No 26) | 5'-GACTGTTTCGGTCTCGGATCTAACTCCTCT-3' |
| N102F + S104L reverse (SEQ ID No 27) | 5'-AGATCCGAGACCGAAACAGTCGAGCACTCG-3' |
| N102F + S104L + N107I forward (SEQ ID No 28) | 5'-TGTTTCGGTCTCGGATCTATCTCCTCTGTC-3' |
| N102F + S104L + N107I reverse (SEQ ID No 29) | 5'-AGGAGATAGATCCGAGACCGAAACAGTCGA-3' |
| N102F + S104L + S106T + N107I forward (SEQ ID No 30) | 5'-TGTTTCGGTCTCGGAACTATCTCCTCTGTC-3' |
| N102F + S104L + S106T + N107I reverse (SEQ ID No 31) | 5'-AGGAGATAGTTCCGAGACCGAAACAGTCGA-3' |
| G132I forward (SEQ ID No 32) | 5'-TCCCTGATTGGAGGCGCTTCTACC-3' |
| G132I reverse (SEQ ID No 33) | 5'-AGCGCCTCCAATCAGGGACATGTT-3' |

TABLE 1-continued

Forward and reverse primers used for site-directed mutagenesis of the gene coding for parent protease for the production of protease variants of the invention

| | Sequences |
|---|---|
| G134K forward (SEQ ID No 34) | 5'-GGTGGAAAGGCTTCTACCGCTCTG-3' |
| G134K reverse (SEQ ID No 35) | 5'-GGTAGAAGCCTTTCCACCCAGGGA-3' |
| N102S + S106T forward (SEQ ID No 36) | 5'-TGTAGCGGTTCCGGAACTAACTCCTCTGTCATC-3' |
| N102S + S106T reverse (SEQ ID No 37) | 5'-AGGAGTTAGTTCCGGAACCGCTACAGTCGAGCACT-3' |
| N102S + N107T forward (SEQ ID No 38) | 5'-TGTAGCGGTTCCGGATCTACCTCCTCTGTCATC-3' |
| N102S + N107T reverse (SEQ ID No 39) | 5'-AGGAGGTAGATCCGGAACCGCTACAGTCGAGCACT-3' |
| S106T + N107T forward (SEQ ID No 40) | 5'-TGTAACGGTTCCGGAACTACCTCCTCTGTCATC-3' |
| S106T + N107T reverse (SEQ ID No 41) | 5'-AGGAGGTAGTTCCGGAACCGTTACAGTCGAGCACT-3' |

Mutated codons are underlined

—Expression and Purification of the Proteases

Recombinant expression of the strains expressing the wild-type protease and its variants was realized in 50 mL ZYM5052 auto inducible medium at 23° C. during 24 hours (Studier et al., 2005—Prot. Exp. Pur. 41, 207-234). The cultures have been stopped by centrifugation (8000 rpm, 20 minutes at 10° C.) in an Avanti J-26 XP centrifuge (Beckman Coulter, Brea, USA). The cells have been frozen at −80° C. during at least 2.5 hours and then suspended in 10 mL of Tris HCl buffer (Tris 0.1 M, pH 7.5). Lysonase™ Bioprocessing Reagent (EMD Millipore) has been used to lysate the cells, according to supplier's recommendation. Then, cell suspension was centrifuged during 30 minutes at 11000 rpm and at 10° C. The soluble fraction has been collected and submitted to cobalt affinity chromatography using Talon® Metal Affinity resin (Clontech, Calif., USA). Protein has been eluted with 100 mM imidazole in 20 mM Tris-HCl, 300 mM NaCl, pH 8.0. Imidazole has been removed from purified extracts after a dialysis step against Tris HCl buffer pH-regulated at 45° C. (Tris 0.1 M, 5 mM $CaCl_2$, pH 7.5). Purified protein has been quantified using Bio-Rad Bradford protein assay according to manufacturer instructions (Lifescience Bio-Rad, France) and stored at +4° C. The quality of the purification has been assessed on SDS-PAGE after TCA precipitation, the expected protein size being around 29 kDa.

Example 2

Evaluation of the Specific Degrading Activity of Proteases

The specific degrading activities of the wild-type protease and variants have been determined during PLA hydrolysis. 50 mg of a 500 µm PLA powder (PLLA 001—Natureplast) were weighed and introduced in dialysis tubing. The enzymatic sample, 1.5 mL of protease preparation containing a fixed concentration of enzyme (66.7 mg/L, 30 mg/L, 10 mg/L or 5 mg/L in order to measure the accurate specific activity), was then added in the dialysis tubing before closing it and this latter was introduced in a glass bottle containing 25 mL of 0.1 M Tris-HCl buffer pH 7.5 (regulated at 45° C.) containing 5 mM of $CaCl_2$. The wild-type protease (SEQ ID No 1) was used as a control.

The depolymerization started by incubating each sample at 45° C. and 150 rpm in a Max Q 4450 incubator (Thermo Fisher Scientific, Inc. Waltham, Mass., USA).

Initial rate of the depolymerization reaction in g of lactic acid and dimers of lactic acid generated/g of enzyme/hour was determined by samplings performed at different times during the first 24 hours and analyzed by Ultra High Performance Liquid Chromatography (UHPLC). If necessary, samples were diluted in 0.1 M Tris-HCl buffer pH 7.5. After filtration on 0.45 µm syringe filter, samples were loaded on UHPLC to monitor the liberation of lactic acid and dimers of lactic acid. Chromatography system used was an Ultimate 3000 UHPLC system (Thermo Fisher Scientific, Inc. Waltham, Mass., USA) including a pump module, an autosampler, a column oven thermostated at 50° C., and a UV detector at 210 nm. The column used was an Aminex HPX-87H (300 mm×7.8 mm), equipped with precolumn, (Supelco, Bellefonte, USA). Lactic acid and dimers of lactic acid were separated using a mobile phase $H_2SO_4$ 5 mM, at a flow rate of 0.5 mL·min$^{-1}$. Injection was 20 µL of sample. Lactic acid and dimers of lactic acid were measured according to standard curves prepared from commercial lactic acid (Sigma-Aldrich L1750-10G) and in house synthetized dimers of lactic acid in the same conditions than samples. The specific degrading activity of PLA hydrolysis (g of equivalent lactic acid (i.e. g of lactic acid and dimer of lactic acid)/hour/g of enzyme) was determined in the linear part of the hydrolysis curve.

The results of the different experiments are shown in the Table 2.

TABLE 2

Specific degrading activity of the wild-type protease (SEQ ID no 1) and variants.

| Wild-type protease or Variant (V) of the invention | Average Specific degrading activity (g equivalent LA·h$^{-1}$·g$^{-1}$) ± standard deviation | Improvement factor in degrading activity vs WT degrading activity |
|---|---|---|
| Wild-type | 10.1 ± 1.9 | / |
| V1: N102F | 42.8 | 4 |
| V2: S104L | 106.9 ± 6.6 | 11 |
| V3: N107I | 20.6 | 2 |
| V4: G132I | 48.5 | 5 |
| V5: G134K | 23.3 | 2 |
| V6: Y167R | 95.7 ± 1.7 | 9.5 |
| V7: S104L + N107I | 261.3 | 26 |
| V8: S104L + Y167R | 555.2 ± 3.8 | 55 |
| V9: D160E + Y167R | 35.8 ± 9.2 | 4 |
| V10: N102S + S106T + N107T + Y167R | 45.1 | 5 |
| V11: N102F + S104L + D160E + Y167R | 603.8 | 60 |
| V12: N102F + S104L + N107I + D160E + Y167R | 720 | 71 |
| V13: N102S + S106T + N107T + D160E + Y167R | 118.4 ± 11.9 | 12 |
| V14: N102F + S106T + N107T + D160E + Y167R | 579 | 57 |
| V15: N102F + S104L + S106T + N107I + D160E + Y167R | 1574 ± 264 | 156 |
| V16: N102F + S104L + S106T + N107I | 1322 ± 136 | 131 |
| V17: N102F + S104L + S106T + N107I + G132I + D160E + Y167R | 1540 ± 0.2 | 153 |
| V18: N102F + S104L + S106T + N107I + Y167R | 1683 ± 78 | 167 |
| V19: N102F + S104L + S106T + N107I + G132I | 1924 | 191 |
| V20: N102S + D160E + Y167R | 95 | 9 |
| V21: S106T + D160E + Y167R | 113 | 11 |
| V22: N107T + D160E + Y167R | 86 | 8.5 |
| V23: N102S + S106T + D160E + Y167R | 71.9 | 7 |
| V24: S106T + N107T + D160E + Y167R | 120.6 | 12 |
| V25: N102S + N107T + D160E + Y167R | 92.9 | 9 |
| V26: N102F + S104L + S106T + N107I + G132I + Y167R | 1406 ± 18 | 139 |

Example 3

Evaluation of the Specific Degrading Activity of Proteases of the Invention

The specific degrading activity of proteases of the invention was determined and compared to the specific degrading activity of the wild-type protease of SEQ ID No 1.

Multiple methodologies to assess the specific activity have been used:
(1) Specific degrading activity based upon the pNA hydrolysis;
(2) Specific degrading activity based upon the degradation of a polyester (PLA) under solid form;
(3) Specific degrading activity based upon the decrease of the turbidity of an emulsion containing PLA;
(4) Specific degrading activity based upon PLA hydrolysis in reactors.

3.1 pNA Hydrolysis

20 μL of protein in solution has been combined to 180 μL of 5 mM N-succinyl-Ala-Ala-Ala-p-nitroanilide (pNA) into Tris HCl buffer, 0.1M pH7.5 (regulated at 30° C.). Enzymatic reaction has been performed at 30° C. under agitation, during at least 15 minutes and absorbance at 405 nm acquired by microplate spectrophotometer (Versamax, Molecular Devices, Sunnyvale, Calif., USA) in order to quantify the pNA release during the reaction. Specific activity (initial velocity expressed in absorbance at 405 nm (A405 nm) per min and per mg of enzyme) has been determined in the linear part of the hydrolysis curve and used to assay the protease activity of the wild type protease or the variants. A solution of 20 μL 0.1M Tris HCl buffer pH7.5, containing no enzyme has been used as a negative control reaction.

The specific activity of variant V18 has been evaluated at 21.5 A405 nm.min-1.mg-1. This shows that the protease variant V18 is able to degrade the pNA and thus conserves it protease activity.

3.2 Degradation of a Polyester Under Solid Form

20 μL of enzyme preparation was deposited in a well created in an agarose plate containing PLA. Preparation of agarose plates was realized by solubilizing 450 mg of PLA in 10 mL dichloromethane (DCM) and homogenizing with a vortex. After addition of 90 mL of Tris HCl buffer 0.1 M pH 7-9 followed by a sonication step (Fisher Scientific™ Model 705 Sonic Dismembrator, at 30% of maximum power), DCM has been evaporated at 50° C. The resulting solution has been filtered to remove the undissolved residues. Finally, 12 mL of the 0.5% PLA emulsion was mixed with 3 mL of 1 M Tris HCl buffer pH 7.5 (regulated at 45° C.) and 15 mL of agarose 2%, to prepare each omnitray (stored at 4° C.).

The diameters of the halos formed due to the polyester degradation by wild-type protease and variants were measured and compared after 4 to 24 hours at 45° C.

3.3 Specific Activity Based Upon the Decrease of the Turbidity of an Emulsion Containing PLA PLA-degrading enzyme activity was assayed based on the decrease of turbidity at wavelength of 630 nm at 45° C. for 30 min, and pH 7.5 (regulated at 45° C.) with a final concentration of 0.1% (w/v) emulsified PLA in 100 mM Tris-HCl buffer (pH 7.5.), (using an Sonic Dismembrator, at 30% of maximum power). One unit of the PLA-degrading activity was defined as a 1 unit decrease in optical density per min under the assay condition described.

PLA Hydrolysis in Reactor

A Minibio 500 bioreactors (Applikon Biotechnology B.V., Delft, The Netherlands) was started with 5 g of PLA and 100 mL of 100 mM Tris-HCl buffer pH 7.5 (regulated at 45° C.) containing 2.5 to 10 mg of protease. Agitation was set at 250 rpm using a marine impeller. Bioreactor was thermostated at 45° C. by immersion in an external water bath. pH was regulated at 7.5 by addition of KOH at 3 M. The different parameters (pH, temperature, agitation, addition of base) were monitored thanks to BioXpert software V2.95. 500 μL of reaction medium was sampled regularly.

Amount of LA and dimers of LA were determined by HPLC, as described in example 2.

Specific activity corresponds to specific rate of degradation, and is calculated in mg of total liberated LA and dimers of LA per hour and per mg of enzyme.

Example 4

Evaluation of the Thermostability of Protease Variants

Different methodologies were used to estimate thermostability:

(1) Residual polyester's depolymerization activity after protein incubation in given conditions of temperatures, times and buffers;

(2) Circular dichroism of proteins in solution.

4.1 Residual Polyester's Degrading Activity

The thermal stabilities of the wild type protease and variants of the invention were determined by measurement of the residual specific degrading activity (PLA hydrolysis as described in Example 2) recovered after a heat shock. The heat shocks were performed as follow: an enzymatic sample containing a fixed enzyme concentration (0.2 or 0.1 g/L) in 0.1 M Tris-HCl buffer pH 7.5 (regulated at 45° C.), 20 mM of CaCl$_2$, was immersed in a water-bath adjusted at a fixed temperature (70° C., 75° C., 85° C. or 98° C.) during a given time (5, 30, 45, 60 or 240 minutes). The samples were immediately placed on ice after the heat shock. After a step of dilution of the enzyme (up to 0.03 g/L or 0.01 g/L), the specific degrading activities (PLA hydrolysis) recovered after the heat shocked and non-heat shocked samples were measured as detailed in Example 2 (buffer: Tris-HCl 0.1 M pH7.5; CaCl$_2$) concentration: 5 mM). The results of residual degrading activities are expressed as a percentage of the specific activity of the reference condition which corresponds to the non-heat shocked sample.

a. Thermal stability of the wild-type protease (SEQ ID No 1) and of variant V14 (N102F+S106T+N107T+D160E+Y167R)

Heat shock conditions and residual degrading activity results after heat shock are showed in Table 3. For these experiments, the specific degrading activity was assessed with an enzyme concentration of 0.03 g/L.

TABLE 3

Residual degrading activities of the wild-type protease and variant V14 of the invention after heat shock.

| Heat shock conditions | Heat shock duration | Wild type Residual Degrading Activity (%) | Variant V14 Residual Degrading Activity (%) |
|---|---|---|---|
| 70° C. Enzyme concentration: 0.1 g/L | 30 minutes | 118 | 101 |
| | 60 minutes | 105 | 103 |
| 75° C. Enzyme concentration: 0.2 g/L | 30 minutes | 86 | 77 |
| | 60 minutes | 58 | 65 |
| | 240 minutes | 48 | 38 |
| 85° C. Enzyme concentration: 0.2 g/L | 30 minutes | 60 | 47 |
| 98° C. Enzyme concentration: 0.2 g/L | 5 minutes | 39 | 43 |

Table 3 shows that the protease variant V14 retains a degrading activity after treatment at high temperatures. Particularly the protease variant of the invention retains polyester degrading activity after heat shock at temperature above 70° C.

b. Thermal stability of the protease variants V14 (N102F+S106T+N107T+D160E+Y167R), V16 (N102F+S104L+S106T+N107I) and V15 (N102F+S104L+S106T+N107I+D160E+Y167R)

Heat shock conditions and residual activity results after heat shock are shown in Table 4 below. For these experiments, the specific activity was assessed with an enzyme concentration of 0.01 g/L.

TABLE 4

Residual degrading activities of protease variants of the invention after heat shock.

| Heat shock conditions | Heat shock duration | V14 Residual Degrading Activity (%) | V16 Residual Degrading Activity (%) | V15 Residual Degrading Activity (%) |
|---|---|---|---|---|
| 70° C. Enzyme concentration: 0.2 g/L | 60 minutes | 100 | 99 | 102 |
| 85° C. Enzyme concentration: 0.2 g/L | 45 minutes | 0.6 | 6 | 12 |

Table 4 shows that the protease variants of the invention retain a polyester degrading activity after treatment at high temperatures. In particular, the protease variants of the invention hold about 100% of residual activity after 60 minutes at 70° C.

4.2 Circular Dichroism

Circular dichroism (CD) was performed on a J-815 CD spectrometer (JASCO) to determine and compare the melting temperature ($T_m$) of the protease of SEQ ID No 1 and protease variants of the invention. The $T_m$ corresponds to the temperature at which 50% of the protein is denatured.

Protein sample was prepared at 0.2 mg/mL in buffer containing 100 mM Tris-HCl pH7.5 (regulated at 45° C.). Experiments were performed in 1 mm optical path quartz cuvette (Starna Scientific Ltd, UK) and far-UV (195-260) CD spectra were first measured to determine two maxima intensities of CD corresponding to the correct folding of the protein.

Thermal denaturation curves of the proteins were obtained by monitoring the change in CD values at 220 nm as the temperature was increased. The rate of temperature increase was 1.5° C.min-1. The temperature of the midpoint of the transition, $T_m$, was calculated by curve fitting of the resultant CD values versus temperature data on the basis of a least-squares analysis using Sigmaplot version 11.0 software.

The $T_m$ obtained reflects the thermostability of the given protein. The higher the $T_m$ is, the more stable the variant is at high temperature. The Tm of the wild-type protease of SEQ ID No 1 has been evaluated at 82.4° C.+/−0.2° C.

Compared thermostabilities of protease variants of the invention are shown in Table 5 below, expressed in Tm values. The loss or gain of Tm, as compared to Tm of the wild-type protease which is considered as 100%, is indicated in brackets.

TABLE 5

Tm of protease variants of the invention

| Variant of the invention | Tm | Variation of Tm (%) |
|---|---|---|
| V15 | 78.9° C. +/− 0.3° C. (−3.5° C.) | −4% |
| V17 | 80.4° C. +/− 0.3° C. (−2.0° C.) | −2% |
| V18 | 81.9° C. +/− 0.4° C. (−0.5° C.) | −1% |
| V26 | 85.6° C. +/− 0.2° C. (+3.2° C.) | +4% |

The results show that the Tm of the protease variants V15 (N102F+S104L+S106T+N107I+D160E+Y167R), V17 (N102F+S104L+S106T+N107I+G132I+D160E+Y167R) and V18 (N102F+S104L+S106T+N107I+Y167R) is slightly impaired since the Tm of these variants corresponds to more than 95% of the Tm of the wild-type protease. The Tm of the variant of the invention V26 (N102F+S104L+S106T+N107I+G132I+Y167R) is improved compared to the wild-type protease and corresponds to 104% of the Tm of the wild-type protease.

Example 5

Biodegradable Polyester Material Containing a Protease of the Invention

—Plastic Compound Preparation Through an Extrusion Process

A plastic compound formulation including a protease variant of the invention was prepared and compared to a plastic compound formulation including a commercial enzyme (Savinase®). Both formulations are listed in Table 6. Percentages are given by weight, based on the total weight of the formulation.

TABLE 6

Plastic compound formulations

|   | PLA | Enzymatic formulation | Protease tested |
|---|---|---|---|
| A | 90% | 10% | Savinase ® 16L |
| B | 90% | 10% | V16 |

Formulation B corresponds to the plastic compound containing the variant V16 (N102F+S104L+S106T+N107I) of the invention.

Formulation A corresponds to the control containing commercial enzyme. In the present experiment, the commercial enzyme is Savinase® 16L, from Novozyme, under solid form, which is known to degrade PLA (Degradation of Polylactide by commercial proteases; Y. Oda et al. 2000).

In order to compare the results, each enzymatic formulation contains the same amount of pure enzyme (2.1% by weight, based on the total weight of the enzymatic formulation).

The formulations were prepared using:
PLA (polylactic acid polymer, PLA 4043D from NatureWorks), under a powder form (<1 mm) obtained from PLA pellets immersed in liquid nitrogen and micronized using an Ultra Centrifugal Mill ZM 200 system.
Solid Form of Savinase® 16L, obtained from commercial liquid form by ultrafiltration on 3.5 kDa membrane, diafiltration, addition of gum Arabic (from Nexira) and drying by freeze-drying.
Solid form of variant V16 was obtained from fermentation process, followed by purification on cobalt-column, diafiltration, addition of gum arabic and drying by freeze-drying.

Based on these formulations, biodegradable polylactic acid-based plastic compositions have been prepared through an extrusion process. A compounding machine, or co-rotating twin-screw extruder, has been used ("Haake MiniLab II ThermoFisher"). This compounding machine comprised successively a manual feed element, two co-rotating screws and the head of the twin screw.

All powders were mixed together by manual shaking before introduction in the compounding machine. The mix was then introduced in the feeding zone, and push into the screw extruder applying manual pressure. The mix went through co-rotating screws using a rotation speed of the twin-screw of 80 RPM. The temperature of the extrusion was fixed to 165° C. The mix of PLA and protease then arrived in the screw head, comprising one hole of 0.4 mm in diameter, wherein the mix was pushed in order to form strip shapes. This extrudate was then cut with cutting pliers to obtain the plastic composition under granulated form, i.e. a plastic compound.

—Tests of Biodegradability of the Plastic Compositions

The biodegradability of the plastic compounds obtained above has been assessed.

100 mg of each granulated sample A and B were weighted and introduced in dialysis tubing. 3 mL of 0.1 M Tris-HCl buffer pH 8 were added in the dialysis tubing before closing it. The dialysis tubing was then introduced in a plastic bottle containing 50 mL of 0.1 M Tris-HCl buffer pH 8.

The depolymerization was started by incubating each sample at 28° C. or 45° C., 150 rpm in an Infors HT Multitron Pro incubation shaker. Aliquots of 1 mL of buffer were sampled regularly, filtered on 0.22 μm syringe filter, and analyzed by High Pressure Liquid Chromatography (HPLC) with an Aminex HPX-87H column to monitor the liberation of lactic acid (LA) and lactic acid dimer (DP2). Chromatography system used was an Ultimate 3000 UHPLC system (Thermo Fisher Scientific, Inc. Waltham, Mass., USA) including a pump module, an autosampler, a column oven thermostated at 50° C., and an UV detector at 220 nm. Eluent was 5 mM $H_2SO_4$. Injection was 20 μL of sample. Lactic acid and dimers of lactic acid were measured according to standard curves prepared from commercial lactic acid (Sigma-Aldrich L1750-10G) and in house synthetized dimers of lactic acid in the same conditions than samples.

Hydrolysis of plastic articles was calculated based on LA and dimers of LA released. Percentage of degradation was calculated by the molar ratio of LA plus the LA contained in dimers of LA at a given time versus the LA contained initially in the PLA in the plastic composition. Results of depolymerization, after 10 days of reaction at 28° C. or after 24 hours of reaction at 45° C., are shown in Table 7.

TABLE 7

Depolymerization of plastic compounds including Savinase ® 16L or variant V16 of the invention, after 10 days of reaction at 28° C. and after 24 hours of reaction at 45° C.

|   | Depolymerization at 28° C. (%) after 10 days | Depolymerization at 45° C. (%) after 24 hours |
|---|---|---|
| A (including Savinase ® 16L) | 7% | 0.3% |
| B (including variant V16) | 87% | 84% |

The results show a higher degradation of the plastic composition containing the protease variant V16 compared to the one containing the commercial enzyme. These results indicate higher PLA-degrading activity and/or higher thermostability of the variant of the invention.

The invention claimed is:

1. A protease variant which (i) has at least 85% identity to the full length amino acid sequence set forth in SEQ ID NO: 1, (ii) has at least one amino acid substitution at a position selected from S104, N102, S106, N107, G132, G134, D160, or Y167, wherein the positions are numbered by reference to the amino acid sequence set forth in SEQ ID NO: 1, and (iii) exhibits a polyester degrading activity.

2. The protease variant according to claim 1, wherein said protease comprises at least one amino acid substitution at position S104, wherein the position is numbered by reference to the amino acid sequence set forth in SEQ ID NO: 1.

3. The protease variant according to claim 1, wherein said protease comprises at least one amino acid substitution selected from N102S/F, S104L, S106T, N107T/I, G132I, G134K, D160E and Y167R.

4. The protease variant according to claim 3, wherein said protease comprises at least one amino acid substitution selected from S106T and S104L.

5. The protease variant according to claim 1, wherein said protease comprises at least one combination of substitutions selected from the group consisting of S104L+N107I, S104L+Y167R, D160E+Y167R, N102S+D160E+Y167R, S106T+D160E+Y167R, N107T+D160E+Y167R, N102S+S106T+D160E+Y167R, S106T+N107T+D160E+Y167R, N102S+N107T+D160E+Y167R, N102S+S106T+N107T+Y167R, N102F+S104L+S106T+N107I, N102F+S104L+D160E+Y167R, N102F+S104L+N107I+D160E+Y167R, N102S+S106T+N107T+D160E+Y167R, N102F+S104L+S106T+N107I+Y167R, N102F+S104L+S106T+N107I+G132I, N102F+S106T+N107T+D160E+Y167R, N102F+S104L+S106T+N107I+D160E+Y167R, N102F+S104L+S106T+N107I+G132I+Y167R, and N102F+S104L+S106T+N107I+G132I+D160E+Y167R, wherein the positions are numbered by reference to the amino acid sequence set forth in SEQ ID NO: 1.

6. The protease variant according to claim 1, wherein said protease comprises a single amino acid substitution selected from N102S/F, S104L, S106T, N107T/I, G132I, G134K, D160E, and Y167R.

7. The protease variant according to claim 6, wherein said protease comprises a single amino acid substitution selected from S104L and Y167R.

8. The protease variant according to claim 1, wherein said protease comprises an additional sequence at the N-terminal end an amino acid sequence which has 100% identity to the full length amino acid sequence set forth in SEQ ID NO: 42.

9. The protease variant according to claim 1, wherein said protease comprise an additional amino sequence at the N-terminal end, said additional amino acid sequence having at least 85% identity to the full length amino acid sequence set forth in SEQ ID NO: 42 and at least one amino acid substitution at a position selected from R24, Y75, D106, Q107, E108, V109, R110, A111, and F112, wherein the positions are numbered by reference to the amino acid sequence set forth in SEQ ID NO: 42.

10. An expression cassette or vector comprising a nucleic acid encoding a protease variant as defined in claim 1.

11. A host cell comprising an expression cassette or vector of claim 10.

12. A composition comprising the protease variant as defined in claim 1.

13. A method of producing a protease according to claim 1 comprising:
    (a) culturing a host cell comprising a nucleic acid encoding a protease variant as defined in claim 1 under conditions suitable to express the nucleic acid encoding said protease.

14. The method of producing a protease according to claim 13, further comprising:
    (b) recovering said protease from the cell culture.

15. A method of degrading a plastic product containing at least one polyester comprising:
    (a) contacting the plastic product with a protease according to claim 1, suitable for degrading said at least one polyester in order to degrade said at least one polyester up to monomers and oligomers.

16. The method according to claim 15 further comprising the step of:
    (b) recovering monomers and/or oligomers.

17. The method according to claim 15, wherein the plastic product comprises at least one polyester selected from polylactic acid (PLA), polytrimethylene terephthalate (PTT), polybutylene terephthalate (PBT), polyethylene isosorbide terephthalate (PEIT), polyethylene terephthalate (PET) polyhydroxyalkanoate (PHA), polybutylene succinate (PBS), polybutylene succinate adipate (PBSA), polybutylene adipate terephthalate (PBAT), polyethylene furanoate (PEF), polycaprolactone (PCL), poly(ethylene adipate) (PEA) and blends/mixtures of these materials.

18. A plastic compound containing a protease of claim 1 and at least one polyester.

19. The plastic compound according to claim 18, comprising at least polylactic acid.

20. A masterbatch composition, containing a protease of claim 1 and at least one polyester.

* * * * *

UNITED STATES PATENT AND TRADEMARK OFFICE
CERTIFICATE OF CORRECTION

PATENT NO. : 10,829,754 B2
APPLICATION NO. : 16/470295
DATED : November 10, 2020
INVENTOR(S) : Marty et al.

Page 1 of 1

It is certified that error appears in the above-identified patent and that said Letters Patent is hereby corrected as shown below:

In the Specification

Column 2,
Line 16, "410of the" should read --410 of the-.

Column 2,
Lines 51-52, "N107T+D160E+Y167R, N102S+N107T+D160E+Y167R N102S+S106T+N107T+Y167R," should read --N107T+D160E+Y167R, N102S+S106T+D160E+Y167R, S106T+N107T+D160E+Y167R, N102S+N107T+D160E+Y167R,--.

Column 8,
Line 18, "N102F+S104L+5106T+N107I." should read --N102F+S104L+S106T+N1071.--.

Column 8,
Lines 27-28, "N102F+S104L+5106T+N107I+G132I." should read --N102F+S104L+S106T+N107I+G132I.--.

Column 8,
Lines 31-32, "N102F+S104L+5106T+N107I+G134K+Y167R" should read --N102F+S104L+S106T+N107I+G134K+Y167R--.

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 44

<210> SEQ ID NO 1
<211> LENGTH: 278
<212> TYPE: PRT
<213> ORGANISM: Thermus sp. strain Rt41A

<400> SEQUENCE: 1

```
Ala Val Gln Ser Pro Ala Thr Trp Gly Leu Asp Arg Ile Asp Gln Arg
 1               5                  10                  15

Thr Leu Pro Leu Asp Gly Arg Tyr Thr Tyr Thr Ala Thr Gly Ala Gly
            20                  25                  30

Val His Ala Tyr Val Val Asp Thr Gly Ile Leu Leu Ser His Gln Glu
        35                  40                  45

Phe Thr Gly Arg Ile Gly Lys Gly Tyr Asp Ala Ile Thr Pro Gly Gly
    50                  55                  60

Ser Ala Gln Asp Cys Asn Gly His Gly Thr His Val Ala Gly Thr Ile
65                  70                  75                  80

Gly Gly Thr Thr Tyr Gly Val Ala Lys Gly Val Thr Leu His Pro Val
                85                  90                  95

Arg Val Leu Asp Cys Asn Gly Ser Gly Ser Asn Ser Ser Val Ile Ala
            100                 105                 110

Gly Leu Asp Trp Val Thr Gln Asn His Val Lys Pro Ala Val Ile Asn
        115                 120                 125

Met Ser Leu Gly Gly Gly Ala Ser Thr Ala Leu Asp Thr Ala Val Met
    130                 135                 140

Asn Ala Ile Asn Ala Gly Val Thr Val Val Ala Ala Gly Asn Asp
145                 150                 155                 160

Asn Arg Asp Ala Cys Phe Tyr Ser Pro Ala Arg Val Thr Ala Ala Ile
                165                 170                 175

Thr Val Gly Ala Thr Thr Ser Thr Asp Tyr Arg Ala Ser Phe Ser Asn
            180                 185                 190

Tyr Gly Arg Cys Leu Asp Leu Phe Ala Pro Gly Gln Ser Ile Thr Ser
        195                 200                 205

Ala Trp Tyr Thr Ser Ser Thr Ala Thr Asn Thr Ile Ser Gly Thr Ser
    210                 215                 220

Met Ala Thr Pro His Val Thr Gly Ala Ala Ala Leu Tyr Leu Gln Trp
225                 230                 235                 240

Tyr Pro Thr Ala Thr Pro Ser Gln Val Ala Ser Ala Leu Leu Tyr Tyr
                245                 250                 255

Ala Thr Pro Asn Val Val Lys Asn Ala Gly Arg Tyr Ser Pro Asn Leu
            260                 265                 270

Leu Leu Tyr Thr Pro Phe
        275
```

<210> SEQ ID NO 2
<211> LENGTH: 1170
<212> TYPE: DNA
<213> ORGANISM: artificial sequence
<220> FEATURE:
<223> OTHER INFORMATION: sequence encoding propeptide and protease

<400> SEQUENCE: 2

```
aaccctcccg ctgcttccac ccaggaagct ccctgctgg gcctggaggc tcctgaggct    60
atccccggcc gatacattgt cgtctacaag gagaacgctg acgtgctgcc tgctctggag   120
gctctcaagg ctgctctgga gcctggtctc atgcagcctc aggactgca ggctcaggct   180
```

```
ctccgaaccc tcggcctgga gggtgctcga gtggacaagg tctacaccgc tgctctgcga    240
ggtgtggctg tggaggtgcc tgaccaggag ctggctcgac tccgacagga cccccgagtg    300
gcttacatcg aggccgacca ggaagtccga gctttcgccg tgcagtctcc tgctacctgg    360
ggtctggacc gaattgacca gcgaaccctc cccctggacg gacgatacac ctacaccgct    420
accggtgctg gagtccacgc ctacgtcgtg gacaccggca tcctgctctc ccaccaggag    480
ttcaccggtc gaatcggcaa gggttacgac gctattaccc ccggcggttc tgctcaggac    540
tgcaacggac acggcaccca cgtggctggc accattggag gcaccaccta cggagtggct    600
aagggtgtga ccctgcaccc cgtccgagtg ctcgactgta acggttccgg atctaactcc    660
tctgtcatcg ctggtctgga ctgggtgacc cagaaccacg tcaagcccgc cgtgattaac    720
atgtccctgg gtgaggcgc ttctaccgct ctggacaccg ccgtcatgaa cgctatcaac    780
gctggtgtga ccgtggtggt ggctgctggt aacgacaacc gagacgcttg tttctactct    840
cccgctcgag tcaccgctgc tattaccgtg ggagctacca cctctaccga ctaccgagcc    900
tccttctcta actacggtcg atgtctcgac ctgttcgccc ccggacagtc catcacctct    960
gcttggtaca cctcctctac cgccaccaac accatttccg gaacctctat ggctacccct    1020
cacgtgaccg gtgccgctgc cctctacctg cagtggtacc ctaccgctac cccttcccag    1080
gtggcttctg ccctgctcta ctacgctacc cccaacgtgg tcaagaacgc cggccgatac    1140
tcccccaacc tgctcctcta cacccccttc    1170
```

```
<210> SEQ ID NO 3
<211> LENGTH: 23
<212> TYPE: DNA
<213> ORGANISM: artificial sequence
<220> FEATURE:
<223> OTHER INFORMATION: N102S forward primer

<400> SEQUENCE: 3
ctcgactgta gcggttccgg atc                                             23

<210> SEQ ID NO 4
<211> LENGTH: 23
<212> TYPE: DNA
<213> ORGANISM: artificial sequence
<220> FEATURE:
<223> OTHER INFORMATION: N102S reverse primer

<400> SEQUENCE: 4
gatccggaac cgctacagtc gag                                             23

<210> SEQ ID NO 5
<211> LENGTH: 24
<212> TYPE: DNA
<213> ORGANISM: artificial sequence
<220> FEATURE:
<223> OTHER INFORMATION: S106T forward primer

<400> SEQUENCE: 5
tccggaacta actcctctgt catc                                            24

<210> SEQ ID NO 6
<211> LENGTH: 24
<212> TYPE: DNA
<213> ORGANISM: artificial sequence
<220> FEATURE:
<223> OTHER INFORMATION: S106T reverse primer
```

<400> SEQUENCE: 6
ggagttagtt ccggaaccgt taca                                       24

<210> SEQ ID NO 7
<211> LENGTH: 20
<212> TYPE: DNA
<213> ORGANISM: artificial sequence
<220> FEATURE:
<223> OTHER INFORMATION: N107T forward primer

<400> SEQUENCE: 7
ccggatctac ctcctctgtc                                            20

<210> SEQ ID NO 8
<211> LENGTH: 20
<212> TYPE: DNA
<213> ORGANISM: artificial sequence
<220> FEATURE:
<223> OTHER INFORMATION: N107T reverse primer

<400> SEQUENCE: 8
gacagaggag gtagatccgg                                            20

<210> SEQ ID NO 9
<211> LENGTH: 22
<212> TYPE: DNA
<213> ORGANISM: artificial sequence
<220> FEATURE:
<223> OTHER INFORMATION: D160E forward primer

<400> SEQUENCE: 9
gctggtaacg aaaaccgaga cg                                         22

<210> SEQ ID NO 10
<211> LENGTH: 22
<212> TYPE: DNA
<213> ORGANISM: artificial sequence
<220> FEATURE:
<223> OTHER INFORMATION: D160E reverse primer

<400> SEQUENCE: 10
cgtctcggtt ttcgttacca gc                                         22

<210> SEQ ID NO 11
<211> LENGTH: 35
<212> TYPE: DNA
<213> ORGANISM: artificial sequence
<220> FEATURE:
<223> OTHER INFORMATION: Y167R forward primer

<400> SEQUENCE: 11
cgagacgctt gtttccgctc tcccgctcga gtcac                           35

<210> SEQ ID NO 12
<211> LENGTH: 33
<212> TYPE: DNA
<213> ORGANISM: artificial sequence
<220> FEATURE:
<223> OTHER INFORMATION: Y167R reverse primer

<400> SEQUENCE: 12
gaaacaagcg tctcggttgt cgttaccagc agc                             33

<210> SEQ ID NO 13
<211> LENGTH: 38

<210> SEQ ID NO 13
<211> LENGTH: 38
<212> TYPE: DNA
<213> ORGANISM: artificial sequence
<220> FEATURE:
<223> OTHER INFORMATION: D160E+Y167R forward primer

<400> SEQUENCE: 13
taacgaaaac cgagacgctt gtttccgctc tcccgctc                   38

<210> SEQ ID NO 14
<211> LENGTH: 40
<212> TYPE: DNA
<213> ORGANISM: artificial sequence
<220> FEATURE:
<223> OTHER INFORMATION: D160E+Y167R reverse primer

<400> SEQUENCE: 14
gggagagcgg aaacaagcgt ctcggttttc gttaccagca                 40

<210> SEQ ID NO 15
<211> LENGTH: 33
<212> TYPE: DNA
<213> ORGANISM: artificial sequence
<220> FEATURE:
<223> OTHER INFORMATION: N102S+S106T+N107T forward primer

<400> SEQUENCE: 15
tgtagcggtt ccggaactac ctcctctgtc atc                        33

<210> SEQ ID NO 16
<211> LENGTH: 35
<212> TYPE: DNA
<213> ORGANISM: artificial sequence
<220> FEATURE:
<223> OTHER INFORMATION: N102S+S106T+N107T reverse primer

<400> SEQUENCE: 16
aggaggtagt tccggaaccg ctacagtcga gcact                      35

<210> SEQ ID NO 17
<211> LENGTH: 24
<212> TYPE: DNA
<213> ORGANISM: artificial sequence
<220> FEATURE:
<223> OTHER INFORMATION: N102F forward

<400> SEQUENCE: 17
gactgtttcg gttccggatc taac                                  24

<210> SEQ ID NO 18
<211> LENGTH: 24
<212> TYPE: DNA
<213> ORGANISM: artificial sequence
<220> FEATURE:
<223> OTHER INFORMATION: N102F forward mutated

<400> SEQUENCE: 18
gactgtttcg gttccggaac tacc                                  24

<210> SEQ ID NO 19
<211> LENGTH: 23
<212> TYPE: DNA
<213> ORGANISM: artificial sequence
<220> FEATURE:
<223> OTHER INFORMATION: N102F reverse

<400> SEQUENCE: 19
ggaaccgaaa cagtcgagca ctc                                         23

<210> SEQ ID NO 20
<211> LENGTH: 24
<212> TYPE: DNA
<213> ORGANISM: artificial sequence
<220> FEATURE:
<223> OTHER INFORMATION: S104L forward

<400> SEQUENCE: 20
aacggtctcg gatctaactc ctct                                        24

<210> SEQ ID NO 21
<211> LENGTH: 24
<212> TYPE: DNA
<213> ORGANISM: artificial sequence
<220> FEATURE:
<223> OTHER INFORMATION: S104L reverse

<400> SEQUENCE: 21
agatccgaga ccgttacagt cgag                                        24

<210> SEQ ID NO 22
<211> LENGTH: 24
<212> TYPE: DNA
<213> ORGANISM: artificial sequence
<220> FEATURE:
<223> OTHER INFORMATION: N107I forward

<400> SEQUENCE: 22
ggatctatct cctctgtcat cgct                                        24

<210> SEQ ID NO 23
<211> LENGTH: 24
<212> TYPE: DNA
<213> ORGANISM: artificial sequence
<220> FEATURE:
<223> OTHER INFORMATION: N107I reverse

<400> SEQUENCE: 23
agaggagata gatccggaac cgtt                                        24

<210> SEQ ID NO 24
<211> LENGTH: 29
<212> TYPE: DNA
<213> ORGANISM: artificial sequence
<220> FEATURE:
<223> OTHER INFORMATION: S104L+N107I forward

<400> SEQUENCE: 24
aacggtctcg gatctatctc ctctgtcat                                   29

<210> SEQ ID NO 25
<211> LENGTH: 29
<212> TYPE: DNA
<213> ORGANISM: artificial sequence
<220> FEATURE:
<223> OTHER INFORMATION: S104L+N107I reverse

<400> SEQUENCE: 25
agaggagata gatccgagac cgttacagt                                   29

<210> SEQ ID NO 26
<211> LENGTH: 30
<212> TYPE: DNA
<213> ORGANISM: artificial sequence
<220> FEATURE:
<223> OTHER INFORMATION: N102F+S104L forward

<400> SEQUENCE: 26
gactgtttcg gtctcggatc taactcctct        30

<210> SEQ ID NO 27
<211> LENGTH: 30
<212> TYPE: DNA
<213> ORGANISM: artificial sequence
<220> FEATURE:
<223> OTHER INFORMATION: N102F+S104L reverse

<400> SEQUENCE: 27
agatccgaga ccgaaacagt cgagcactcg        30

<210> SEQ ID NO 28
<211> LENGTH: 30
<212> TYPE: DNA
<213> ORGANISM: artificial sequence
<220> FEATURE:
<223> OTHER INFORMATION: N102F+S104L+N107I forward

<400> SEQUENCE: 28
tgtttcggtc tcggatctat ctcctctgtc        30

<210> SEQ ID NO 29
<211> LENGTH: 30
<212> TYPE: DNA
<213> ORGANISM: artificial sequence
<220> FEATURE:
<223> OTHER INFORMATION: N102F+S104L+N107I reverse

<400> SEQUENCE: 29
aggagataga tccgagaccg aaacagtcga        30

<210> SEQ ID NO 30
<211> LENGTH: 30
<212> TYPE: DNA
<213> ORGANISM: artificial sequence
<220> FEATURE:
<223> OTHER INFORMATION: N102F+S104L+S106T+N107I forward

<400> SEQUENCE: 30
tgtttcggtc tcggaactat ctcctctgtc        30

<210> SEQ ID NO 31
<211> LENGTH: 30
<212> TYPE: DNA
<213> ORGANISM: artificial sequence
<220> FEATURE:
<223> OTHER INFORMATION: N102F+S104L+S106T+N107I reverse

<400> SEQUENCE: 31
aggagatagt tccgagaccg aaacagtcga        30

<210> SEQ ID NO 32
<211> LENGTH: 24
<212> TYPE: DNA
<213> ORGANISM: artificial sequence
<220> FEATURE:
<223> OTHER INFORMATION: G132I forward

<400> SEQUENCE: 32
tccctgattg gaggcgcttc tacc        24

<210> SEQ ID NO 33
<211> LENGTH: 24
<212> TYPE: DNA
<213> ORGANISM: artificial sequence
<220> FEATURE:
<223> OTHER INFORMATION: G132I reverse

<400> SEQUENCE: 33
agcgcctcca atcagggaca tgtt                                          24

<210> SEQ ID NO 34
<211> LENGTH: 24
<212> TYPE: DNA
<213> ORGANISM: artificial sequence
<220> FEATURE:
<223> OTHER INFORMATION: G134K forward

<400> SEQUENCE: 34
ggtggaaagg cttctaccgc tctg                                          24

<210> SEQ ID NO 35
<211> LENGTH: 24
<212> TYPE: DNA
<213> ORGANISM: artificial sequence
<220> FEATURE:
<223> OTHER INFORMATION: G134K reverse

<400> SEQUENCE: 35
ggtagaagcc tttccaccca ggga                                          24

<210> SEQ ID NO 36
<211> LENGTH: 33
<212> TYPE: DNA
<213> ORGANISM: artificial sequence
<220> FEATURE:
<223> OTHER INFORMATION: N102S+S106T forward

<400> SEQUENCE: 36
tgtagcggtt ccggaactaa ctcctctgtc atc                                33

<210> SEQ ID NO 37
<211> LENGTH: 35
<212> TYPE: DNA
<213> ORGANISM: artificial sequence
<220> FEATURE:
<223> OTHER INFORMATION: N102S+S106T reverse

<400> SEQUENCE: 37
aggagttagt tccggaaccg ctacagtcga gcact                              35

<210> SEQ ID NO 38
<211> LENGTH: 33
<212> TYPE: DNA
<213> ORGANISM: artificial sequence
<220> FEATURE:
<223> OTHER INFORMATION: N102S+N107T forward

<400> SEQUENCE: 38
tgtagcggtt ccggatctac ctcctctgtc atc                                33

<210> SEQ ID NO 39
<211> LENGTH: 35
<212> TYPE: DNA
<213> ORGANISM: artificial sequence
<220> FEATURE:
<223> OTHER INFORMATION: N102S+N107T reverse -continued

<400> SEQUENCE: 39
aggaggtaga tccggaaccg ctacagtcga gcact                                    35

<210> SEQ ID NO 40
<211> LENGTH: 33
<212> TYPE: DNA
<213> ORGANISM: artificial sequence
<220> FEATURE:
<223> OTHER INFORMATION: S106T+N107T forward

<400> SEQUENCE: 40
tgtaacggtt ccggaactac ctcctctgtc atc                                      33

<210> SEQ ID NO 41
<211> LENGTH: 35
<212> TYPE: DNA
<213> ORGANISM: artificial sequence
<220> FEATURE:
<223> OTHER INFORMATION: S106T+N107T reverse

<400> SEQUENCE: 41
aggaggtagt tccggaaccg ttacagtcga gcact                                    35

<210> SEQ ID NO 42
<211> LENGTH: 112
<212> TYPE: PRT
<213> ORGANISM: artificial sequence
<220> FEATURE:
<223> OTHER INFORMATION: propeptide

<400> SEQUENCE: 42

Asn Pro Pro Ala Ala Ser Thr Gln Glu Ala Pro Leu Leu Gly Leu Glu
1               5                   10                  15

Ala Pro Glu Ala Ile Pro Gly Arg Tyr Ile Val Val Tyr Lys Glu Asn
            20                  25                  30

Ala Asp Val Leu Pro Ala Leu Glu Ala Leu Lys Ala Ala Leu Glu Pro
        35                  40                  45

Gly Leu Met Gln Pro Gln Gly Leu Gln Ala Gln Ala Leu Arg Thr Leu
    50                  55                  60

Gly Leu Glu Gly Ala Arg Val Asp Lys Val Tyr Thr Ala Ala Leu Arg
65                  70                  75                  80

Gly Val Ala Val Glu Val Pro Asp Gln Glu Leu Ala Arg Leu Arg Gln
                85                  90                  95

Asp Pro Arg Val Ala Tyr Ile Glu Ala Asp Gln Glu Val Arg Ala Phe
            100                 105                 110

<210> SEQ ID NO 43
<211> LENGTH: 22
<212> TYPE: PRT
<213> ORGANISM: artificial sequence
<220> FEATURE:
<223> OTHER INFORMATION: PelB signal peptide

<400> SEQUENCE: 43

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 44
<211> LENGTH: 8

```
<212> TYPE: PRT
<213> ORGANISM: artificial sequence
<220> FEATURE:
<223> OTHER INFORMATION: 6xhistidine tag

<400> SEQUENCE: 44

Leu Glu His His His His His His
1               5
```